United States Patent
Ballette et al.

(10) Patent No.: US 11,858,901 B2
(45) Date of Patent: Jan. 2, 2024

(54) 3-((R)-2-(AMINO-2-PHENYLETHYL)-1-(2-FLUORO-6 TRIFLUOROMETHYL BENZYL)-5-IODO-6-METHYL-1H-PYRIMIDINE-2,4-DIONE OR A SALT THEREOF, PROCESS FOR ITS PREPARATION, AND ITS USE IN THE SYNTHESIS OF ELAGOLIX

(71) Applicant: MOEHS IBERICA, S.L., Barcelona (ES)

(72) Inventors: Roberto Ballette, Barcelona (ES); Oscar Jiménez Alonso, Barcelona (ES); Elena García García, Barcelona (ES); Alicia Dobarro Rodríguez, Barcelona (ES)

(73) Assignee: MOEHS IBERICA, S.L., Barcelona (ES)

( * ) Notice: Subject to any disclaimer, the term of this patent is extended or adjusted under 35 U.S.C. 154(b) by 0 days.

(21) Appl. No.: 17/755,412

(22) PCT Filed: Mar. 10, 2020

(86) PCT No.: PCT/EP2020/056368
§ 371 (c)(1),
(2) Date: Apr. 28, 2022

(87) PCT Pub. No.: WO2021/083554
PCT Pub. Date: May 6, 2021

(65) Prior Publication Data
US 2022/0411382 A1 Dec. 29, 2022

(30) Foreign Application Priority Data
Oct. 30, 2019 (ES) .............................. ES201930956

(51) Int. Cl.
*C07D 239/553* (2006.01)
*C07D 239/557* (2006.01)

(52) U.S. Cl.
CPC ..... *C07D 239/553* (2013.01); *C07D 239/557* (2013.01)

(58) Field of Classification Search
CPC .............. C07D 239/54; C07D 239/553; C07D 239/557
See application file for complete search history.

(56) References Cited

FOREIGN PATENT DOCUMENTS

| CN | 112125855 A | 12/2020 |
|---|---|---|
| WO | WO 2005/007164 A1 | 1/2005 |
| WO | WO 2005/007165 A1 | 1/2005 |
| WO | WO 2009/062087 A1 | 5/2009 |
| WO | WO 2019/115019 A1 | 6/2019 |

OTHER PUBLICATIONS

International Search Report issued in International Application No. PCT/EP2020/056368, dated Sep. 6, 2020.
Klyubin et al., "Dependence of the Electronic Absorption Spectra of Aqueous Solutions of Iodine Monochloride on the Conditions of Dilution and Storage Time", Russian Journal of Physical Chemistry A., 91(4): 645-649 (2017).
Zope et al., "The Kinetics Studies on the Rapid Iodination of Anthranilic Acid by Iodine Monochloride in Aqueous Solution", Research Journal Of Chemistry And Environment, 11(2):43-48 (2007).

*Primary Examiner* — Deepak R Rao
(74) *Attorney, Agent, or Firm* — Knobbe, Martens, Olson & Bear, LLP

(57) ABSTRACT

A new intermediate is useful in the synthesis of elagolix. A process for obtaining the intermediate includes reacting a precursor with iodine monochloride in the presence of an organic solvent. A process for preparing elagolix makes use of the intermediate. The intermediate can be 3-((R)-2-(amino-2-phenylethyl)-1-(2-fluoro-6-trifluoromethylbenzyl)-5-iodo-6-methyl-1H-pyrimidine-2,4-dione or a salt thereof, such as a hydrochloride.

27 Claims, 6 Drawing Sheets

3-((R)-2-(AMINO-2-PHENYLETHYL)-1-(2-FLUORO-6 TRIFLUOROMETHYL BENZYL)-5-IODO-6-METHYL-1H-PYRIMIDINE-2,4-DIONE OR A SALT THEREOF, PROCESS FOR ITS PREPARATION, AND ITS USE IN THE SYNTHESIS OF ELAGOLIX

FIELD OF THE INVENTION

The present invention relates to a new intermediate useful in the synthesis of elagolix, to a process for obtaining said intermediate, to the use of said intermediate for preparing elagolix, and to a process for preparing elagolix making use of said intermediate.

BACKGROUND OF THE INVENTION

Elagolix (Orilissa®) is a gonadotropin-releasing hormone antagonist (GnRH antagonist) medication used in the treatment of pain associated with endometriosis in women in the sodium salt form (compound of formula (V)).

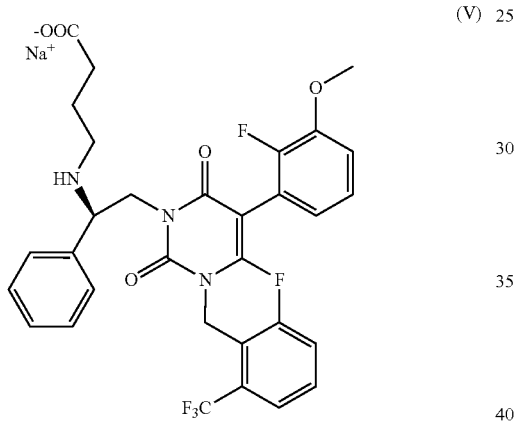

(V)

Elagolix is also under development for treating the uterine myomas in women.

Elagolix was approved by the FDA for treating pain associated with endometriosis in the United States on 23 Jul. 2018. It was the first new medication approved by the FDA for treating endometriosis in over a decade. Elagolix is the first and currently the only marketed member of a new class of GnRH modulators, described as "second generation" due to their non-peptidic small-molecule nature and oral activity.

Several synthetic routes for preparing elagolix sodium (V) have been described, see for example WO 2005/007164 A1, WO 2005/007165 A1, WO 2009/062087 A1, and WO 2019/115019 A1.

The processes described in WO 2005/007164 A1 and WO 2005/007165 A1 comprise the following steps:

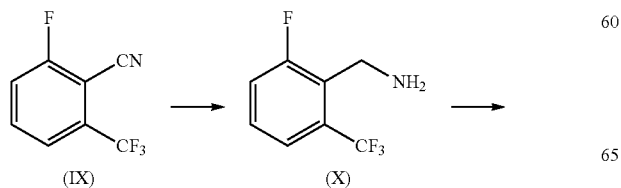

(IX)   (X)

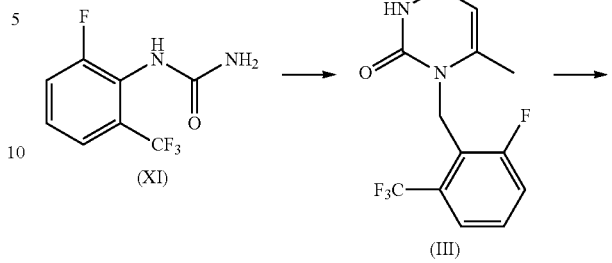

(XI)   (III)

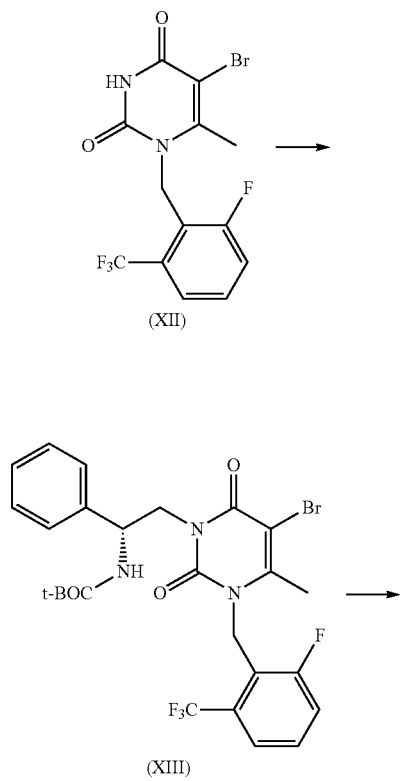

(XII)

(XIII)

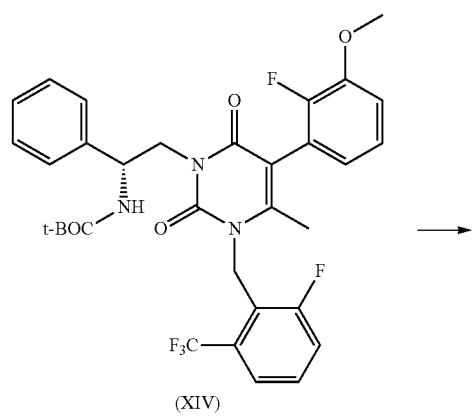

(XIV)

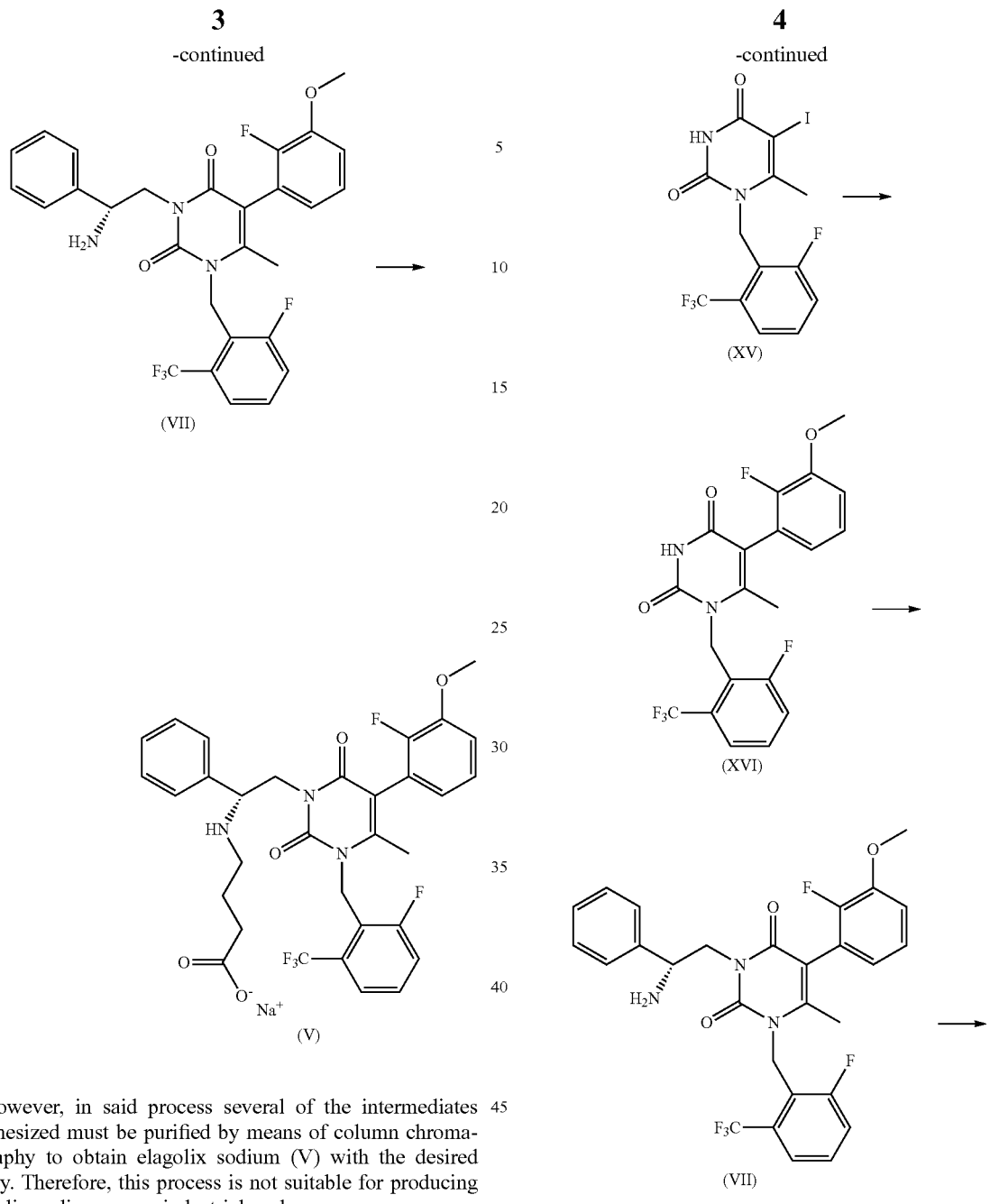
However, in said process several of the intermediates synthesized must be purified by means of column chromatography to obtain elagolix sodium (V) with the desired purity. Therefore, this process is not suitable for producing elagolix sodium on an industrial scale.
The process described in WO 2009/062087 A1 is based in the following reaction steps:
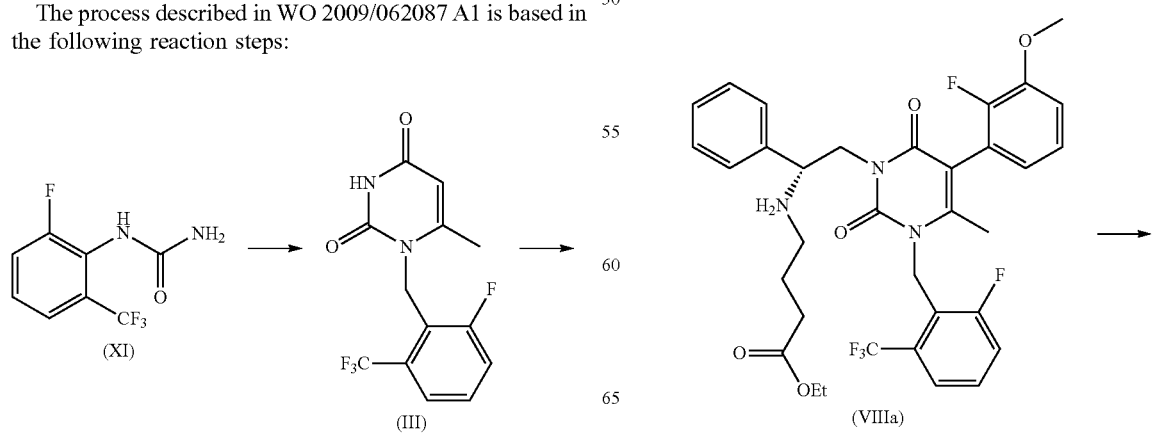

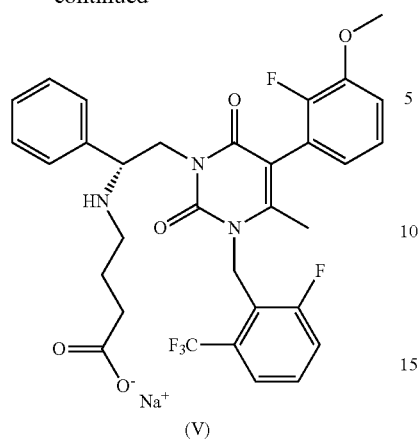

(V)

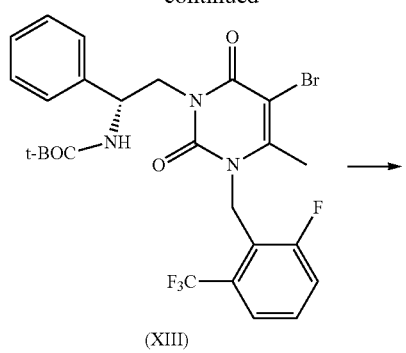

(XIII)

In this process, purification of the intermediates by column chromatography is not performed, so it could be suitable for industrial application. The yield from intermediate (III) until obtaining the intermediate (VIIIa) is not optimal, being 64.2% to 67.3%.

Purification steps by means of column chromatography are not performed in the process described in WO 2019/115019 A1 either, but rather some intermediates are isolated in solid form which can be purified by means of crystallization, in particular intermediates (II) and (XIII). The yield of said process from intermediate (II) to intermediate (VII) is 70.8%.

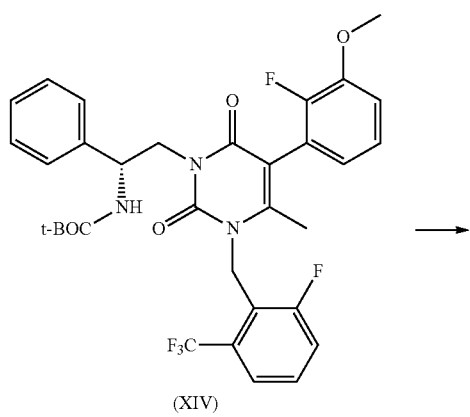

(XIV)

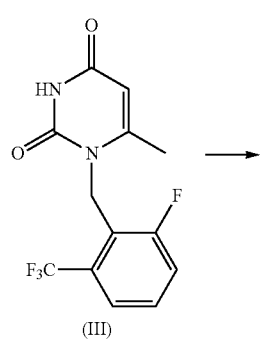

(III)

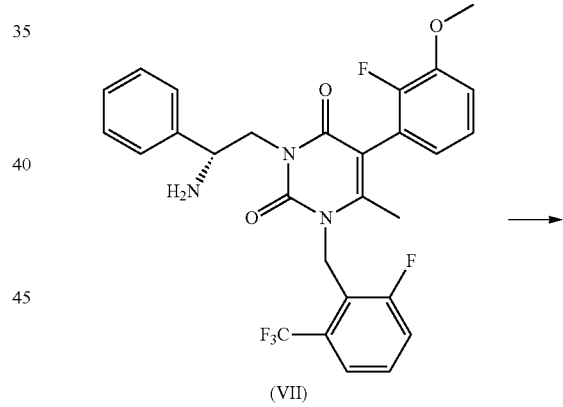

(VII)

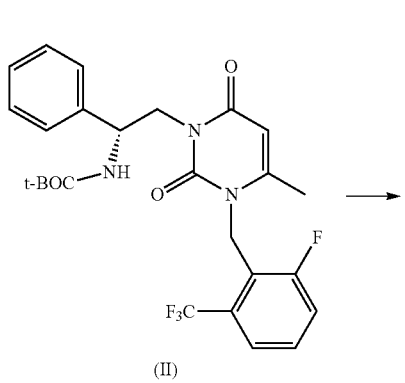

(II)

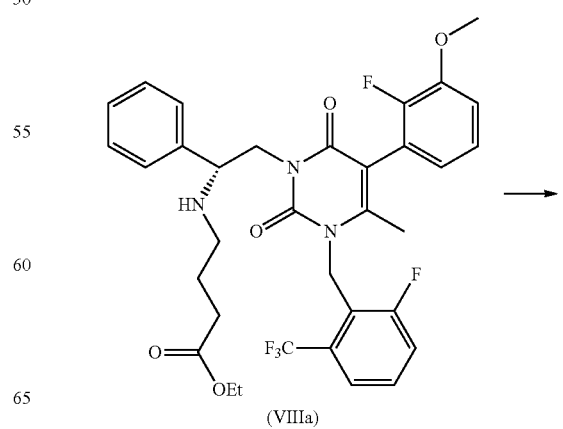

(VIIIa)

-continued

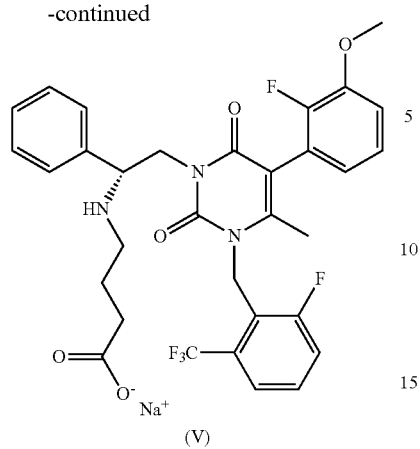

(V)

There is a need in the state of the art for processes for obtaining elagolix sodium with a high level of purity, which allow avoiding the purification of the intermediates by column chromatography and which have high yields.

SUMMARY OF THE INVENTION

The inventors have discovered a new intermediate in the synthesis of elagolix which can be isolated in solid form, thereby facilitating its purification and allowing elagolix to be obtained with a high yield and level of purity.

Therefore, in a first aspect the present invention relates to a compound of formula (I) or a salt thereof.

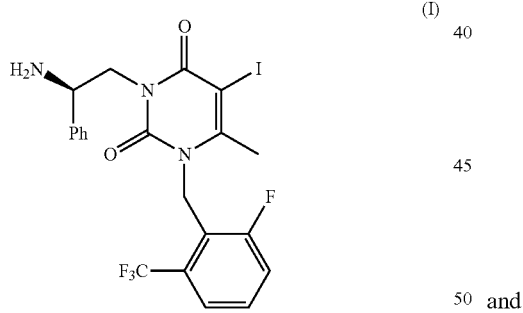

In a second aspect, the present invention relates to a process for preparing a compound of formula (I) or a salt thereof as defined in the first aspect, wherein the process comprises:

a) reacting 3-((R)-2-(tert-butoxycarbonyl)amino-2-phenylethyl)-1-(2-fluoro-6-trifluoromethylbenzyl)-6-methyl-1H-pyrimidine-2,4-dione (II) with iodine monochloride in the presence of an organic solvent to give 3-((R)-2-amino-2-phenylethyl)-1-(2-fluoro-6-trifluoromethylbenzyl)-5-iodo-6-methyl-1H-pyrimidine-2,4-dione hydrochloride (Ia)

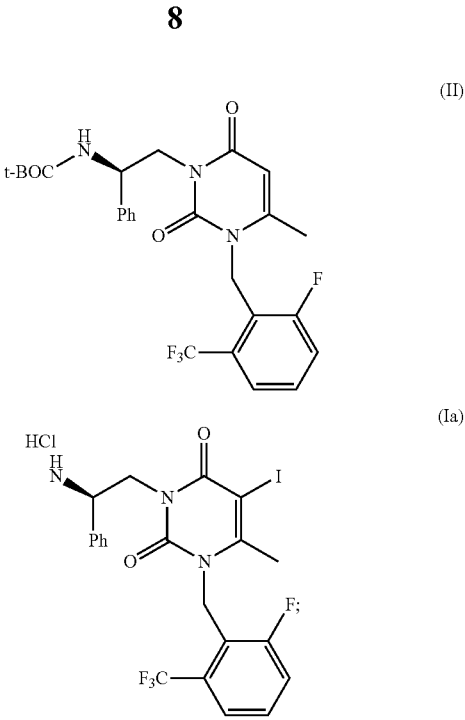

b) optionally treating the 3-((R)-2-(amino-2-phenylethyl)-1-(2-fluoro-6-trifluoromethylbenzyl)-5-iodo-6-methyl-1H-pyrimidine-2,4-dione hydrochloride (Ia) with a base to give the compound of formula (I)

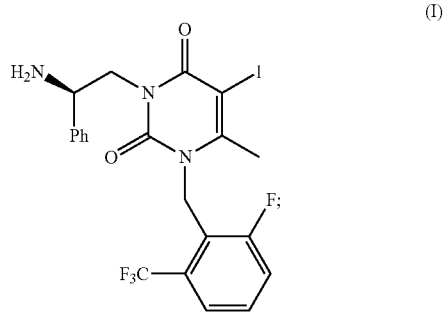

and c) optionally treating the compound of formula (I) with an acid to give a salt of the compound of formula (I).

In a third aspect, the present invention relates to a process for preparing elagolix sodium (V) comprising:

a) reacting the compound of formula (I) or a salt thereof as defined in the first aspect with 2-fluoro-3-methoxyphenylboronic acid (VI) in the presence of a palladium catalyst, a phosphine-type ligand, and a base to give 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII)

(I)

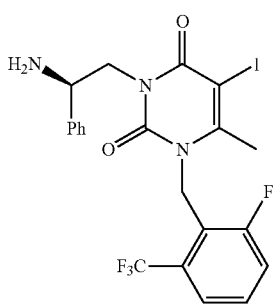

(VI)

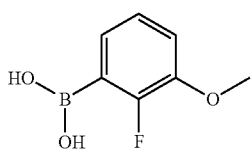

(VII)

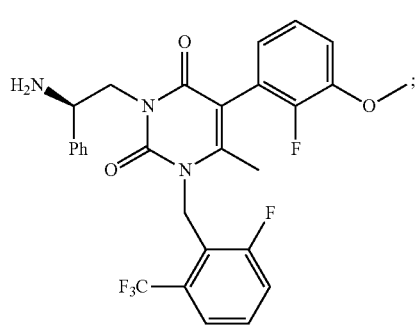

optionally performing steps b1) to b3):
b1) treating the 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII) with HCl to give 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione hydrochloride (VIIa)

(VIIa)

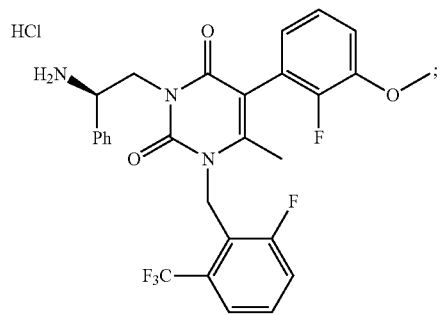

b2) isolating the 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione hydrochloride (VIIa); and b3) treating the 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione hydrochloride (VIIa) with a base to give 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII);

c) reacting the 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII) obtained in step a) or in step b3) with a $C_{1-4}$ alkyl 4-halobutyrate to obtain a compound of formula (VIII)

(VIII)

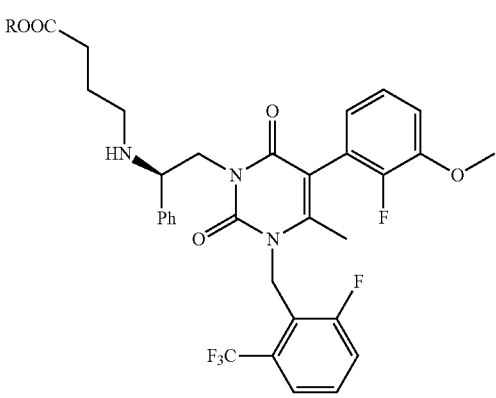

wherein R represents a $C_{1-4}$ alkyl group; and d) hydrolyzing the ester group of the compound of formula (VIII) by treatment with NaOH to obtain elagolix sodium (V)

(V)

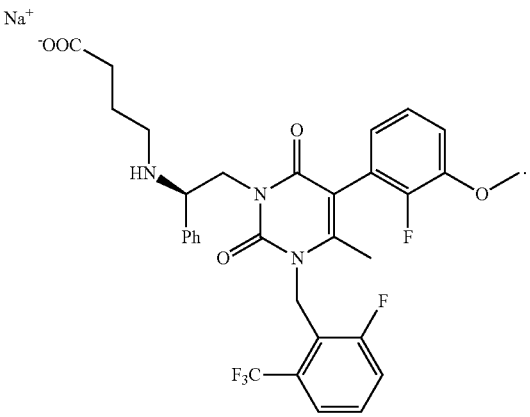

In a fourth aspect, the invention relates to the use of a compound of formula (I) or a salt thereof as defined in the first aspect in a process for preparing elagolix sodium (V).

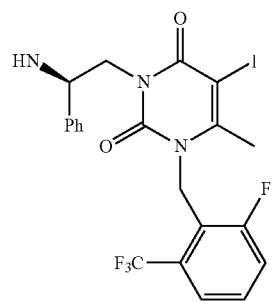

(I)

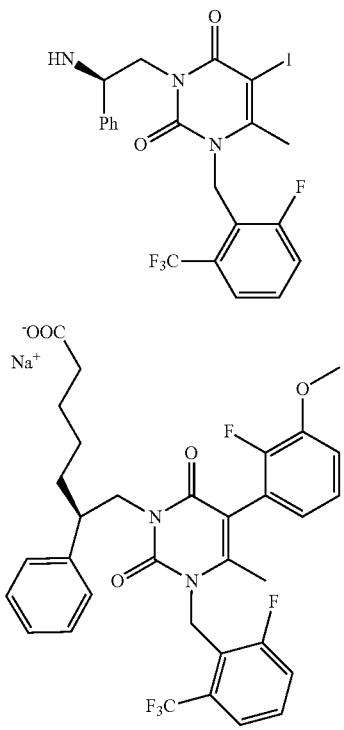

(V)

DETAILED DESCRIPTION OF THE PREFERRED EMBODIMENT

Compound of Formula (I) or a Salt Thereof.

In a first aspect, the present invention relates to a compound of formula (I) (3-((R)-2-(amino-2-phenylethyl)-1-(2-fluoro-6-trifluoromethylbenzyl)-5-iodo-6-methyl-1H-pyrimidine-2,4-dione) or a salt thereof.

(I)

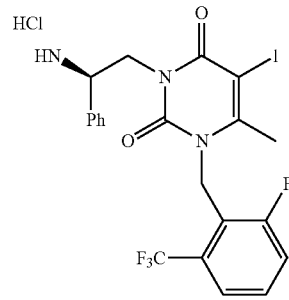

In the context of the invention, the term "salt" must be understood as an ionic compound formed by a cation of the amino group of the compound of formula (I), and a counterion (an anion), such as, for example, an anion of an acid, whether inorganic (such as, for example, hydrochloride, hydrobromide, hydroiodide, sulfate, nitrate, and phosphate, among others) or organic (such as, for example, acetate, trifluoroacetate, maleate, fumarate, citrate, oxalate, succinate, tartrate, malate, mandelate, methanesulfonate, and p-toluenesulfonate, among others). Preferably, the salt of compound (I) is a hydrochloride.

In a preferred embodiment, the compound of the first aspect is 3-((R)-2-(amino-2-phenylethyl)-1-(2-fluoro-6-trifluoromethylbenzyl)-5-iodo-6-methyl-1H-pyrimidine-2,4-dione hydrochloride (Ia).

(Ia)

In a preferred embodiment, said 3-((R)-2-(amino-2-phenylethyl)-1-(2-fluoro-6-trifluoromethyl benzyl)-5-iodo-6-methyl-1H-pyrimidine-2,4-dione hydrochloride (Ia) is in solid form.

In a preferred embodiment, the 3-((R)-2-(amino-2-phenylethyl)-1-(2-fluoro-6-trifluoromethyl benzyl)-5-iodo-6-methyl-1H-pyrimidine-2,4-dione hydrochloride (Ia) has an X-ray powder diffractogram measured with CuKα radiation with peaks at 8.5, 9.9, 14.7, 16.9, 19.5, 21.0, and 22.9° 2θ±0.2°θ.

Figure 2:
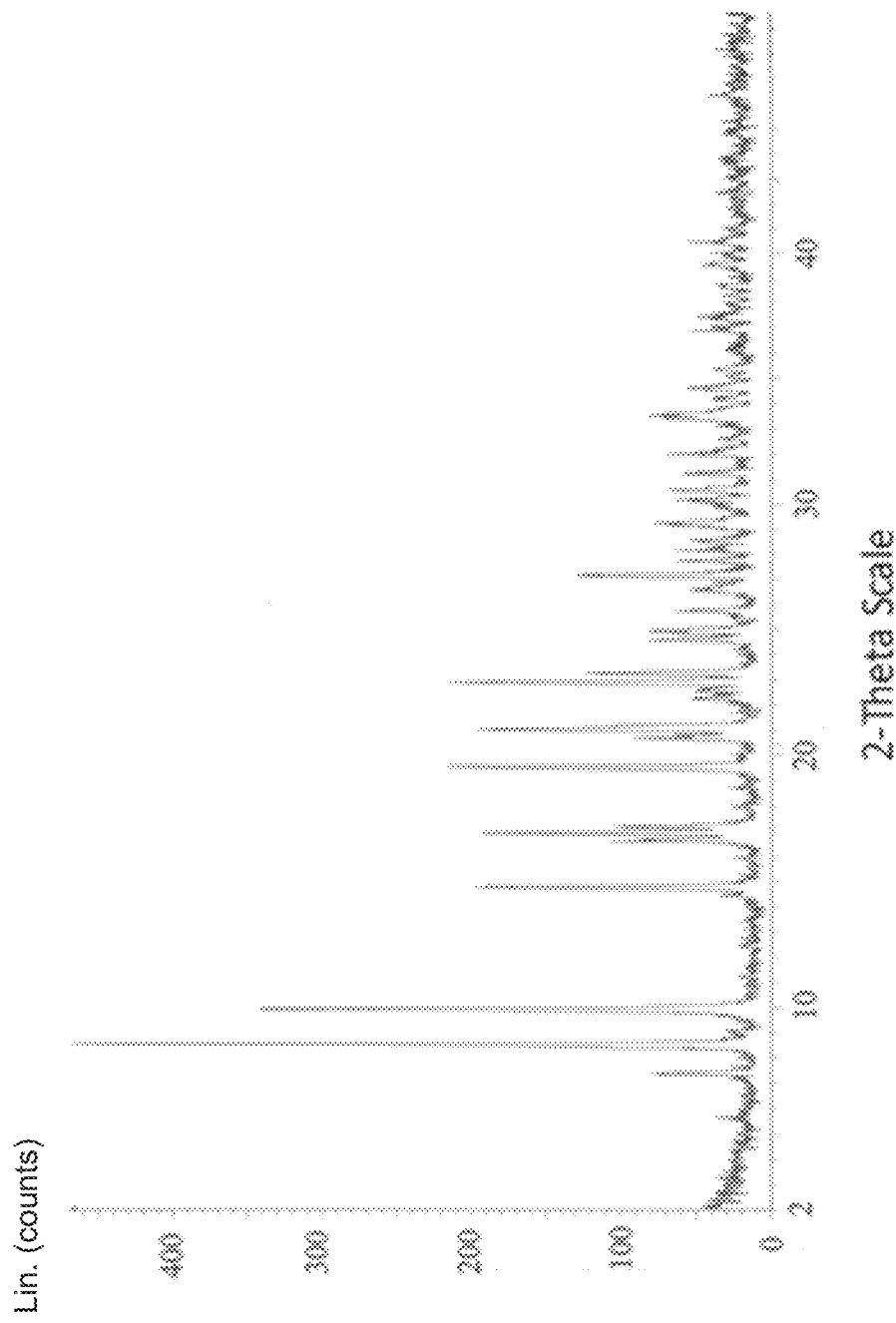
FIG. 2 shows the X-ray powder diffractogram (XRPD) obtained for 3-((R)-2-(amino-2-phenylethyl)-1-(2-fluoro-6-trifluoromethylbenzyl)-5-iodo-6-methyl-1H-pyrimidine-2, 4-dione hydrochloride of Example 2.

In a preferred embodiment, the 3-((R)-2-(amino-2-phenylethyl)-1-(2-fluoro-6-trifluoromethyl benzyl)-5-iodo-6-methyl-1H-pyrimidine-2,4-dione hydrochloride (Ia) has an X-ray powder diffractogram measured with CuKα radiation essentially as that of FIG. 2.

The X-ray diffractograms can be recorded using a powder diffraction system with a copper anode emitting CuKα radiation with a wavelength of 1.54 Å, in particular, following the method described in the examples.

In a preferred embodiment, the 3-((R)-2-(amino-2-phenylethyl)-1-(2-fluoro-6-trifluoromethyl benzyl)-5-iodo-6-methyl-1H-pyrimidine-2,4-dione hydrochloride (Ia) has a differential scanning calorimetry (DSC) diagram comprising an endothermic peak having an onset temperature of about 240.7° C.±2° C. and an exothermic peak having an onset temperature of about 248.6° C.±2° C.

Figure 1:
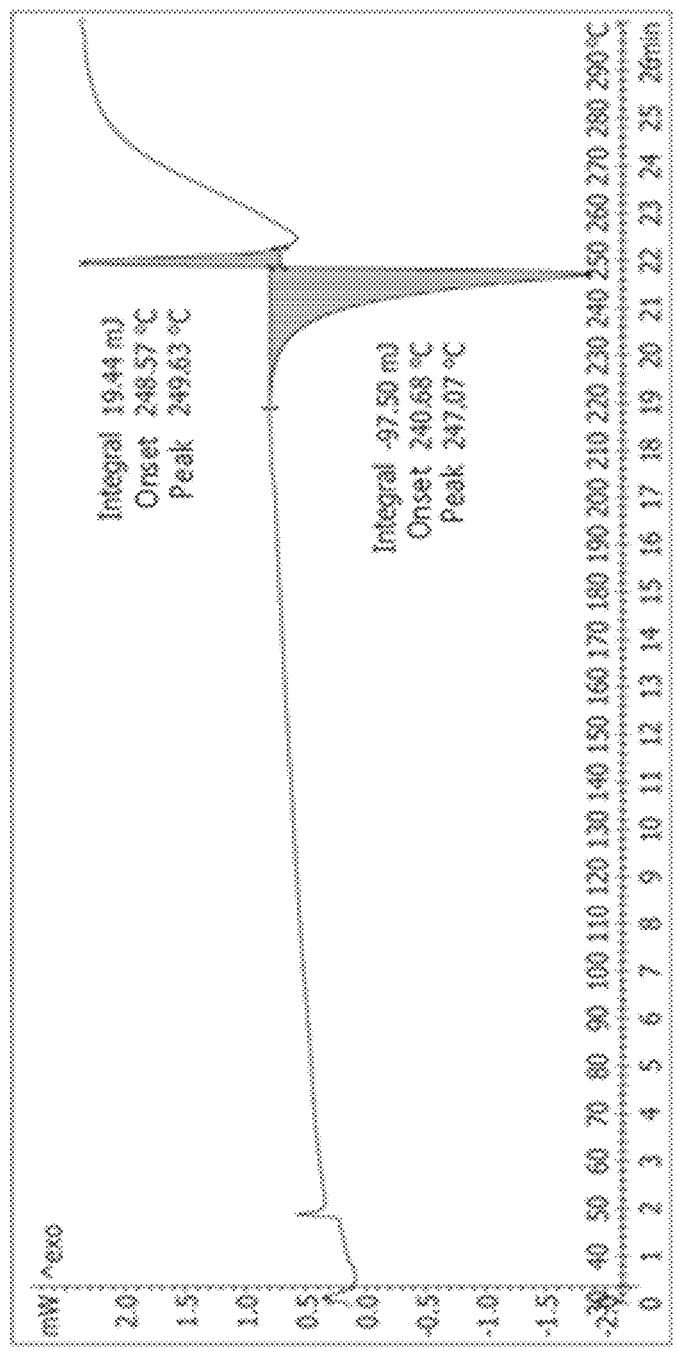
FIG. 1 shows the differential scanning calorimetry (DSC) graph obtained for 3-((R)-2-(amino-2-phenylethyl)-1-(2-fluoro-6-trifluoromethylbenzyl)-5-iodo-6-methyl-1H-pyrimidine-2,4-dione hydrochloride of Example 2.

In a preferred embodiment, the 3-((R)-2-(amino-2-phenylethyl)-1-(2-fluoro-6-trifluoromethyl benzyl)-5-iodo-6-methyl-1H-pyrimidine-2,4-dione hydrochloride (Ia) has a differential scanning calorimetry (DSC) diagram essentially as that of FIG. 1.

The differential scanning calorimetry diagram can be obtained as described in the examples.

The onset temperature or "T onset" refers to the temperature resulting from extrapolating the baseline before the start of the transition and the baseline during energy absorption (tangent to the curve). It can be calculated as defined in standard DIN ISO 11357-1:2016(E).

Process for Preparing the Compound of Formula (I) or a Salt Thereof.

In a second aspect, the present invention relates to a process for preparing a compound of formula (I) or a salt thereof as defined in the first aspect, wherein the process comprises:

a) reacting the 3-((R)-2-(tert-butoxycarbonyl)amino-2-phenylethyl)-1-(2-fluoro-6-trifluoromethyl benzyl)-6-methyl-1H-pyrimidine-2,4-dione (II) with iodine monochloride in the presence of an organic solvent to give 3-((R)-2-(amino-2-phenylethyl)-1-(2-fluoro-6-trifluoromethylbenzyl)-5-iodo-6-methyl-1H-pyrimidine-2,4-dione hydrochloride (Ia)

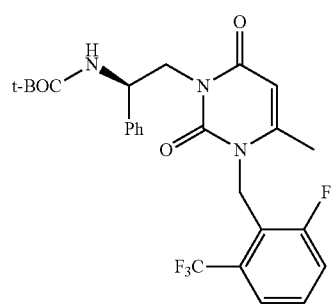

(II)

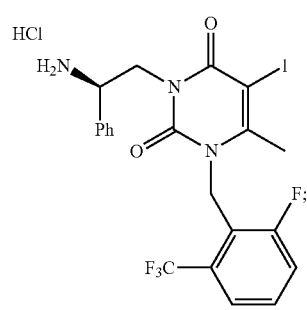

(Ia)

b) optionally treating the 3-((R)-2-(amino-2-phenylethyl)-1-(2-fluoro-6-trifluoromethylbenzyl)-5-iodo-6-methyl-1H-pyrimidine-2,4-dione hydrochloride (Ia) with a base to give the compound of formula (I)

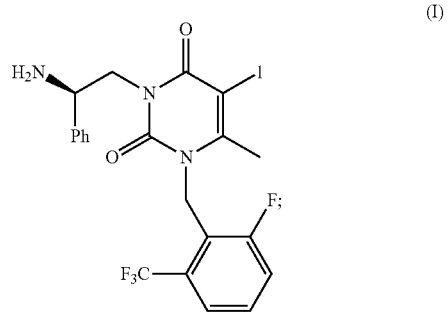

(I)

and c) optionally treating the compound of formula (I) with an acid to give a salt of the compound of formula (I).

Step a) of the process yields 3-((R)-2-(amino-2-phenylethyl)-1-(2-fluoro-6-trifluoromethylbenzyl)-5-iodo-6-methyl-1H-pyrimidine-2,4-dione hydrochloride (Ia).

The organic solvent used in step a) is any organic solvent suitable for carrying out the reaction. Examples of suitable organic solvents are dichloromethane, $C_1$-$C_4$ alkanols, such as methanol, ethanol, n-propanol, isopropanol, n-butanol, sec-butanol, iso-butanol, tert-butanol, and a mixtures thereof; preferably dichloromethane, methanol and mixtures thereof; more preferably methanol; even more preferably a mixture of dichloromethane and methanol.

In a preferred embodiment, in step a) 4 to 8 mL of organic solvent are used with respect to each gram of 3-((R)-2-(tert-butoxycarbonyl)amino-2-phenylethyl)-1-(2-fluoro-6-trifluoromethylbenzyl)-6-methyl-1H-pyrimidine-2,4-dione (II), preferably 5 to 8 mL.

In a preferred embodiment, step a) is performed at a temperature of 45° C. to 55° C., more preferably 48° C. to 52° C. Preferably, it is maintained under stirring in the temperature range indicated of 1.5 to 3 hours.

In a particular embodiment, in step a) at least 2 mol of iodine monochloride are used with respect to each mol of 3-((R)-2-(tert-butoxycarbonyl)amino-2-phenylethyl)-1-(2-fluoro-6-trifluoromethylbenzyl)-6-methyl-1H-pyrimidine-2,4-dione (II), preferably 2 to 4 mol, more preferably 2.5 to 3.5 mol.

In a preferred embodiment, step a) is performed by adding a solution of 3-((R)-2-(tert-butoxycarbonyl)amino-2-phenylethyl)-1-(2-fluoro-6-trifluoromethylbenzyl)-6-methyl-1H-pyrimidine-2,4-dione (II) in the organic solvent, preferably methanol or dichloromethane, to a solution of iodine monochloride in the organic solvent, preferably methanol. The organic solvent of the solution of 3-((R)-2-(tert-butoxycarbonyl)amino-2-phenylethyl)-1-(2-fluoro-6-trifluoromethylbenzyl)-6-methyl-1H-pyrimidine-2,4-dione (II) can be the same as or different from the organic solvent of the solution of iodine monochloride (provided that the solvents are miscible with one another). In a particular embodiment it is the same, for example methanol. In another particular embodiment it is different, for example, dichloromethane is the organic solvent used in the solution of compound (II) and methanol is the organic solvent used in the solution of iodine monochloride.

In a particular embodiment, the concentration of iodine monochloride in the solution of iodine monochloride in the organic solvent is 0.2 to 0.6 g/ml. In particular, the concentration of 3-((R)-2-(tert-butoxycarbonyl)amino-2-phenylethyl)-1-(2-fluoro-6-trifluoromethylbenzyl)-6-methyl-1H-pyrimidine-2,4-dione (II) in the solution of 3-((R)-2-(tert-butoxycarbonyl)amino-2-phenylethyl)-1-(2-fluoro-6-trifluoromethylbenzyl)-6-methyl-1H-pyrimidine-2,4-dione (II) in the organic solvent is 0.2 to 0.8 g/mL, in particular 0.2 to 0.6 g/mL. Preferably, the addition is performed at a temperature of 20° C. to 35° C., more preferably 20° C. to 25° C. After the addition, it is heated at a temperature of 45° C. to 55° C., more preferably 48° C. to 52° C. Preferably, it is maintained under stirring for 1.5 to 3 hours after the addition.

In a particular embodiment, after the formation reaction of 3-((R)-2-(amino-2-phenylethyl)-1-(2-fluoro-6-trifluoromethylbenzyl)-5-iodo-6-methyl-1H-pyrimidine-2,4-dione hydrochloride (Ia) in step a), this salt is isolated from the reaction medium. In particular, it is isolated by removing the solvent. In particular, the solvent can be removed by distillation at a pressure of less than 101325 Pa (less than 1 atm). Preferably, acetone is added after removing the solvent, in particular 2 to 5 ml of acetone are added with respect to each gram of 3-((R)-2-(amino-2-phenylethyl)-1-(2-fluoro-6-trifluoromethylbenzyl)-5-iodo-6-methyl-1H-pyrimidine-2,4-dione hydrochloride (Ia), and the resulting 3-((R)-2-(amino-2-phenylethyl)-1-(2-fluoro-6-trifluoromethylbenzyl)-5-iodo-6-methyl-1H-pyrimidine-2,4-dione hydrochloride (Ia) in solid form is isolated by filtration.

Step b) of the process is optional. Said step is performed to obtain 3-((R)-2-(amino-2-phenylethyl)-1-(2-fluoro-6-trifluoromethylbenzyl)-5-iodo-6-methyl-1H-pyrimidine-2,4-dione (1) in the form of a free base.

Step b) comprises treating the 3-((R)-2-(amino-2-phenylethyl)-1-(2-fluoro-6-trifluoromethylbenzyl)-5-iodo-6-methyl-1H-pyrimidine-2,4-dione hydrochloride (Ia) with a base.

Any base capable of yielding the compound of formula (I) in the form of a free base can be used. Bases suitable for said step b) are, for example, sodium hydroxide, potassium hydroxide, sodium carbonate, potassium carbonate, among others. Preferably said bases are used in solution in water. In particular, at least one mol of base is used with respect to each mol of 3-((R)-2-(amino-2-phenylethyl)-1-(2-fluoro-6-trifluoromethylbenzyl)-5-iodo-6-methyl-1H-pyrimidine-2,4-dione hydrochloride (Ia). In particular, the free base of the compound of formula (I) obtained is isolated by extraction with a water-immiscible organic solvent followed by removing the solvent, preferably by distillation at a pressure of less than 101325 Pa (less than 1 atm).

The expression "water-immiscible organic solvent" refers to an organic solvent that is not water-miscible in at least one proportion of said solvent and water, i.e., in at least one proportion of said solvent and water two phases are produced. The phases can be rapidly identified by means of visual inspection. Miscibility/immiscibility is determined at a temperature in the range of 20° C. to 25° C. Examples of water-immiscible organic solvents are ethyl acetate, butyl acetate, isopropyl acetate, methyl ethyl ketone, methyl tert-butyl ether, diisopropyl ether, dichloromethane, chloroform, cyclohexane, hexane, heptane, pentane, toluene, xylene, and mixtures thereof.

In a particular embodiment, the treatment of step b) is performed for 0.5 h to 2 h. In particular, said treatment is performed at a temperature of 20° C. to 35° C., more preferably 20° C. to 25° C.

Step c) of the process is optional. Said step is performed to obtain a salt of the compound of formula (I), in particular a salt of the compound of formula (I) that is not the hydrochloride, since the hydrochloride is obtained directly in step a) of the process.

Step c) comprises treating the compound of formula (I) in the form of a free base obtained in step b) with an acid to give a salt of the compound of formula (I).

In a particular embodiment, the treatment of step c) is performed for 0.5 h to 2 h. In particular, said treatment is performed at a temperature of 20° C. to 35° C., more preferably 20 to 25° C.

Acids suitable for said step are inorganic acids (such as, for example, HBr, HI, sulfuric acid, nitric acid, and phosphoric acid, among others) or organic acids (such as, for example, acetic acid, trifluoroacetic acid, maleic acid, fumaric acid, citric acid, oxalic acid, succinic acid, tartaric acid, malic acid, mandelic acid, methanesulfonic acid, and p-toluenesulfonic acid, among others). Preferably, the acid is not HCl, since the resulting salt would be the hydrochloride (Ia) which has been obtained in step a).

Preferably said acids are used in solution in water, organic solvent (such as, for example, $C_1$-$C_4$ alkanol), and mixtures thereof. In particular, at least one mol of acid is used with respect to each mol of 3-((R)-2-(amino-2-phenylethyl)-1-(2-fluoro-6-trifluoromethylbenzyl)-5-iodo-6-methyl-1H-pyrimidine-2,4-dione hydrochloride (Ia). In particular, the salt of the compound of formula (I) obtained is isolated by removing the solvent, preferably by distillation at a pressure of less than 101325 Pa (less than 1 atm).

In a preferred embodiment, steps b) and c) are not performed, i.e., the product obtained by the process of the second aspect is 3-((R)-2-(amino-2-phenylethyl)-1-(2-fluoro-6-trifluoromethylbenzyl)-5-iodo-6-methyl-1H-pyrimidine-2,4-dione hydrochloride (Ia).

In another embodiment, step b) is performed and, therefore, the product obtained by the process of the second aspect is 3-((R)-2-(amino-2-phenylethyl)-1-(2-fluoro-6-trifluoromethylbenzyl)-5-iodo-6-methyl-1H-pyrimidine-2,4-dione (I), i.e., in the form of a free base.

In another embodiment, steps b) and c) are performed. Therefore, the product obtained by the process of the second aspect is a 3-((R)-2-(amino-2-phenylethyl)-1-(2-fluoro-6-trifluoromethylbenzyl)-5-iodo-6-methyl-1H-pyrimidine-2,4-dione salt. Preferably, the salt obtained in step c) is not the hydrochloride (Ia).

In a preferred embodiment, the 3-((R)-2-(tert-butoxycarbonyl)amino-2-phenylethyl)-1-(2-fluoro-6-trifluoromethylbenzyl)-6-methyl-1H-pyrimidine-2,4-dione (II) used in step a) is obtained by reacting 1-(2-fluoro-6-trifluoromethylbenzyl)-6-methyl-1H-pyrimidine-2,4-dione (III) with a compound of formula (IV), wherein LG is a leaving group, in an organic solvent, and in the presence of a base.

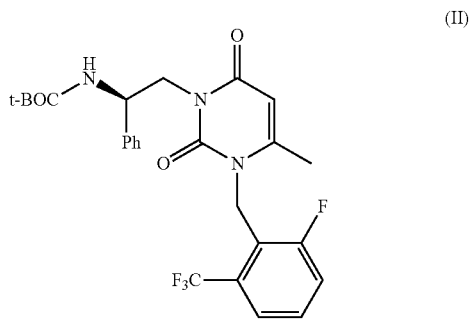

(II)

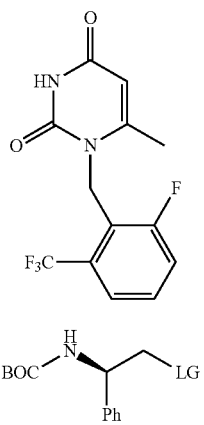

(III)

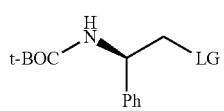

(IV)

The radical "t-BOC", "t-Boc", "BOC", or "Boc" refers to a tert-butoxycarbonyl group.

The leaving group LG of the compound of formula (IV) can be selected from the group consisting of mesylate, tosylate, triflate, iodide, bromide, and chloride. Preferably the leaving group LG of the compound of formula (IV) is mesylate. Therefore, preferably the compound of formula (IV) is (R)-2-((tert-butoxycarbonyl)amino)-2-phenylethyl methanesulfonate (IVa).

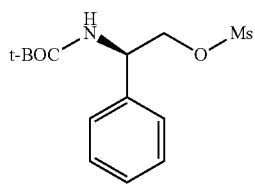

(IVa)

Bases suitable for reacting 1-(2-fluoro-6-trifluoromethyl-benzyl)-6-methyl-1H-pyrimidine-2,4-dione (III) with the compound of formula (IV) are potassium carbonate, sodium carbonate, potassium hydrogen carbonate, sodium hydrogen carbonate, potassium hydroxide, and sodium hydroxide, among others; preferably the base is potassium carbonate ($K_2CO_3$). In a particular embodiment, at least 1 mol of base is used with respect to each mol of compound of formula (III), preferably 1 to 4 mol, more preferably 1 to 2 mol.

Organic solvents suitable for reacting 1-(2-fluoro-6-trifluoromethyl-benzyl)-6-methyl-1H-pyrimidine-2,4-dione (III) with the compound of formula (IV) are ketones (such as, for example, acetone and methyl isobutyl ketone), alcohols (such as, for example, methanol, ethanol, isopropanol, n-butanol, sec-butanol, tert-butanol, 1,2-propanediol, amyl alcohol, and isoamyl alcohol), and esters (such as, for example, ethyl acetate, isopropyl acetate, and tert-butyl acetate), N,N-dimethylformamide (DMF), and mixtures thereof; preferably the organic solvent is selected from the group consisting of acetone, DMF and mixtures thereof; more preferably, the organic solvent is acetone or DMF. In a particular embodiment, 3 to 7 mL of organic solvent are used with respect to each gram of 1-(2-fluoro-6-trifluoromethyl-benzyl)-6-methyl-1H-pyrimidine-2,4-dione (III).

In a particular embodiment, the reaction of 1-(2-fluoro-6-trifluoromethyl-benzyl)-6-methyl-1H-pyrimidine-2,4-dione (III) with the compound of formula (IV) is performed in the presence of a phase-transfer catalyst. Preferably, the phase-transfer catalyst is present when the organic solvent used in the reaction is acetone. Preferably, the phase-transfer catalyst is not present when the organic solvent used in the reaction is DMF. Phase-transfer catalysts suitable are quaternary ammonium salts, such as, for example, tetrabutylammonium iodide and tetramethylammonium iodide; preferably the phase-transfer catalyst is tetrabutylammonium iodide (TBAI). In particular, 0.1 to 0.5 mol of phase-transfer catalyst are used with respect to each mol of 1-(2-fluoro-6-trifluoromethyl-benzyl)-6-methyl-1H-pyrimidine-2,4-dione (III), preferably 0.15 to 0.25 mol.

In a particular embodiment, the reaction of 1-(2-fluoro-6-trifluoromethyl-benzyl)-6-methyl-1H-pyrimidine-2,4-dione (III) with the compound of formula (IV) is performed at a temperature of 50° C. to 70° C. In one embodiment, the reaction is performed at a temperature of 50° C. to 60° C., in particular when the organic solvent used in the reaction is acetone. In another embodiment, the reaction is performed at a temperature of 60° C. to 70° C., in particular when the organic solvent used in the reaction is DMF. Preferably, said treatment is performed for 12 h to 20 h.

The reaction of 1-(2-fluoro-6-trifluoromethyl-benzyl)-6-methyl-1H-pyrimidine-2,4-dione (III) with the compound of formula (IV) yields 3-((R)-2-(tert-butoxycarbonyl)amino-2-phenylethyl)-1-(2-fluoro-6-trifluoromethylbenzyl)-6-methyl-1H-pyrimidine-2,4-dione (II). In a particular embodiment, said compound (II) is isolated by removing the solvent, preferably by distillation at a pressure of less than 101325 Pa (less than 1 atm). After removing the solvent or directly on the reaction mixture (i.e. without performing the step removing the solvent), water and a water-immiscible organic solvent, preferably ethyl acetate and/or tert-butyl methyl ether, are added. Optionally, the pH is adjusted to 7 to 8, preferably by adding aqueous hydrochloric acid. The water-immiscible organic solvent phase is separated, and said solvent is removed, preferably by distillation at a pressure of less than 101325 Pa (less than 1 atm).

Process for Preparing Elagolix Sodium (V)

The third aspect of the invention relates to a process for preparing elagolix sodium (V) comprising:

a) reacting the compound of formula (I) or a salt thereof as defined in the first aspect with 2-fluoro-3-methoxyphenylboronic acid (VI) in the presence of a palladium catalyst, a phosphine-type ligand, and a base to give 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII)

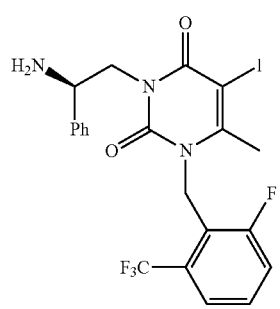

(I)

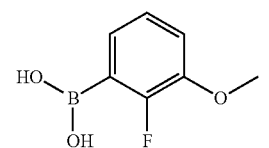

(VI)

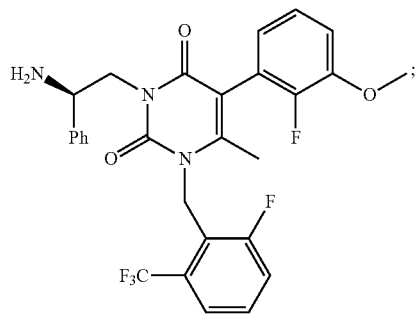

(VII)

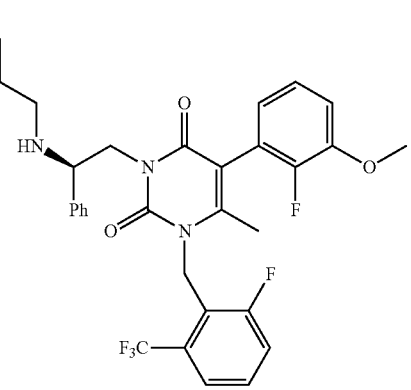

(VIII)

optionally performing steps b1) to b3):

b1) treating the 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII) with HCl to give 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione hydrochloride (VIIa)

wherein R represents a $C_{1-4}$ alkyl group; and d) hydrolyzing the ester group of the compound of formula (VIII) by treatment with NaOH to obtain elagolix sodium (V)

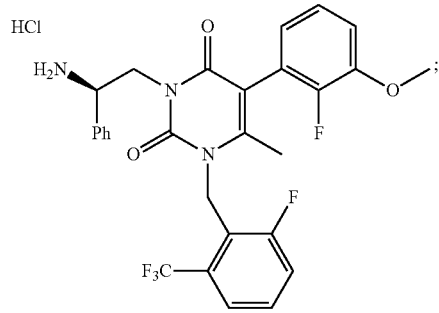

(VIIa)

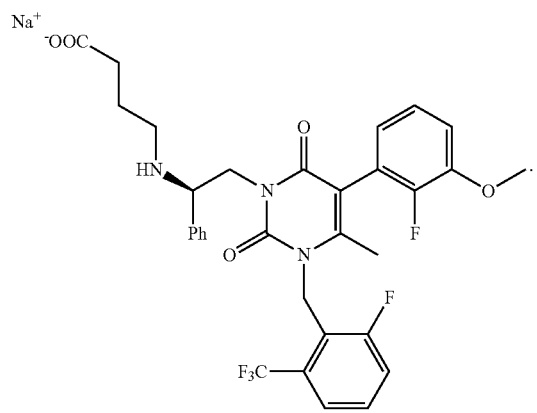

(V)

b2) isolating the 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione hydrochloride (VIIa); and b3) treating the 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione hydrochloride (VIIa) with a base to give 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII);

c) reacting the 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII) obtained in step a) or in step b3) with a $C_{1-4}$ alkyl 4-halobutyrate to obtain a compound of formula (VIII)

Step a) of the process is reacting the compound of formula (I) or a salt thereof as defined in the first aspect with 2-fluoro-3-methoxyphenylboronic acid (VI) in the presence of a palladium catalyst, a phosphine-type ligand, and a base to give 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII). In a preferred embodiment, in step a) the 3-((R)-2-(amino-2-phenylethyl)-1-(2-fluoro-6-trifluoromethylbenzyl)-5-iodo-6-methyl-1H-pyrimidine-2,4-dione hydrochloride (Ia) is reacted.

Palladium catalysts suitable for the reaction are palladium (II) acetate (Pd(OAc)$_2$), palladium(II) bromide and palladium(II) chloride; preferably palladium(II) acetate. In a particular embodiment, in step a) 0.001 to 0.05 mol of palladium catalyst are used with respect to each mol of the compound of formula (I) or a salt thereof, preferably 0.005 to 0.05 mol, more preferably 0.0085 to 0.025 mol.

Phosphine-type ligands suitable for the reaction are tri-tert-butyltetraphosphonium tetrafluoroborate, triphenylphosphine, tricyclohexylphosphine, tri-tert-butylphosphine, tri-n-butylphosphine, tri-n-butylphosphonium tetrafluoroborate, and triethylphosphonium tetrafluoroborate, among others; preferably the phosphine-type ligand is tri-tert-butyltetraphosphonium tetrafluoroborate. In a particular embodiment, in step a) 0.005 to 0.05 mol of phosphine-type ligand are used for each mol of compound of formula (I) or a salt thereof, preferably 0.0085 to 0.025 mol.

Bases suitable for the reaction are potassium phosphate, potassium carbonate, potassium hydroxide, or hydrates thereof, preferably potassium phosphate or a hydrate thereof. In a particular embodiment, in step a) 2 to 6 mol of base are used with respect to each mol of compound of formula (I) or a salt thereof, preferably 3 to 5 mol. In another embodiment, in step a) 2 to 4 mol of base are used with respect to each mol of compound of formula (I) or a salt thereof.

In a preferred embodiment, in step a) the palladium catalyst is palladium(II) acetate, the phosphine-type ligand is tri-tert-butyltetraphosphonium tetrafluoroborate, and/or the base is potassium phosphate or a hydrate thereof. In a more preferred embodiment, in step a) the palladium catalyst is palladium(II) acetate, the phosphine-type ligand is tri-tert-butyltetraphosphonium tetrafluoroborate, and the base is potassium phosphate or a hydrate thereof.

In a particular embodiment, step a) is performed in a suitable solvent. Examples of suitable solvents are mixtures of water and organic solvent (such as acetone, tetrahydrofuran, 2-methyltetrahydrofuran and dioxane); preferably the solvent is a mixture of water and acetone. In a particular embodiment, the proportion by volume of the water and the organic solvent in the mixture is 1:5 to 5:1, preferably 1:2 to 2:1, more preferably about 1:1.

In a particular embodiment, the reaction of step a) is performed at a temperature of 50° C. to 70° C. Preferably, said treatment is performed for 3 h to 24 h. Preferably step a) is performed under inert atmosphere, such as, for example, a nitrogen or argon atmosphere.

The reaction of step a) of the third aspect yields 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII). In a particular embodiment, said compound (VII) is isolated by separating the aqueous phase; treating the remaining organic phase with an aqueous acid solution, preferably with a pH of 1 to 2 (preferably phosphoric acid); separating the organic phase; treating the remaining aqueous phase with a base (preferably potassium carbonate) to a pH of 9 to 10 and with water-immiscible organic solvent (preferably isopropyl acetate); separating the aqueous phase; and removing the organic solvent from the resulting organic phase, preferably by distillation at a pressure of less than 101325 Pa (less than 1 atm).

In a preferred embodiment, step a) further comprises crystallizing the compound (VII) obtained from a suitable solvent, such as, for example, a mixture of acetone and water. In a particular embodiment, the proportion by volume of acetone and water in the mixture is 99:1 to 50:50, preferably 80:20 to 55:45, more preferably 70:30 to 60:40. In another particular embodiment, the proportion by volume of acetone and water in the mixture is from 80:20 to 45:55, preferably 70:30 to 45:55. In another particular embodiment, the proportion by volume of acetone and water is about 2:1. In another particular embodiment, the proportion by volume of acetone and water is about 1:1. In a particular embodiment, 5 to 10 mL of solvent are used with respect to each gram of the compound (VII), preferably 6 to 8 mL of solvent with respect to each gram of the compound (VII).

In a preferred embodiment, the compound of formula (VII) is obtained as a solid, in particular a crystalline solid.

Thus, in another aspect, the invention relates to a compound of formula (VII) in the form of a solid, preferably a crystalline solid.

In a preferred embodiment, the compound of formula (VII) in solid form has an X-ray powder diffractogram measured with CuKα radiation with peaks at 4.6, 9.1, 11.7, 12.2, 13.2, 16.0, 18.2, 18.6, 22.2, 24.7 2θ±0.2°θ.

Figure 4:
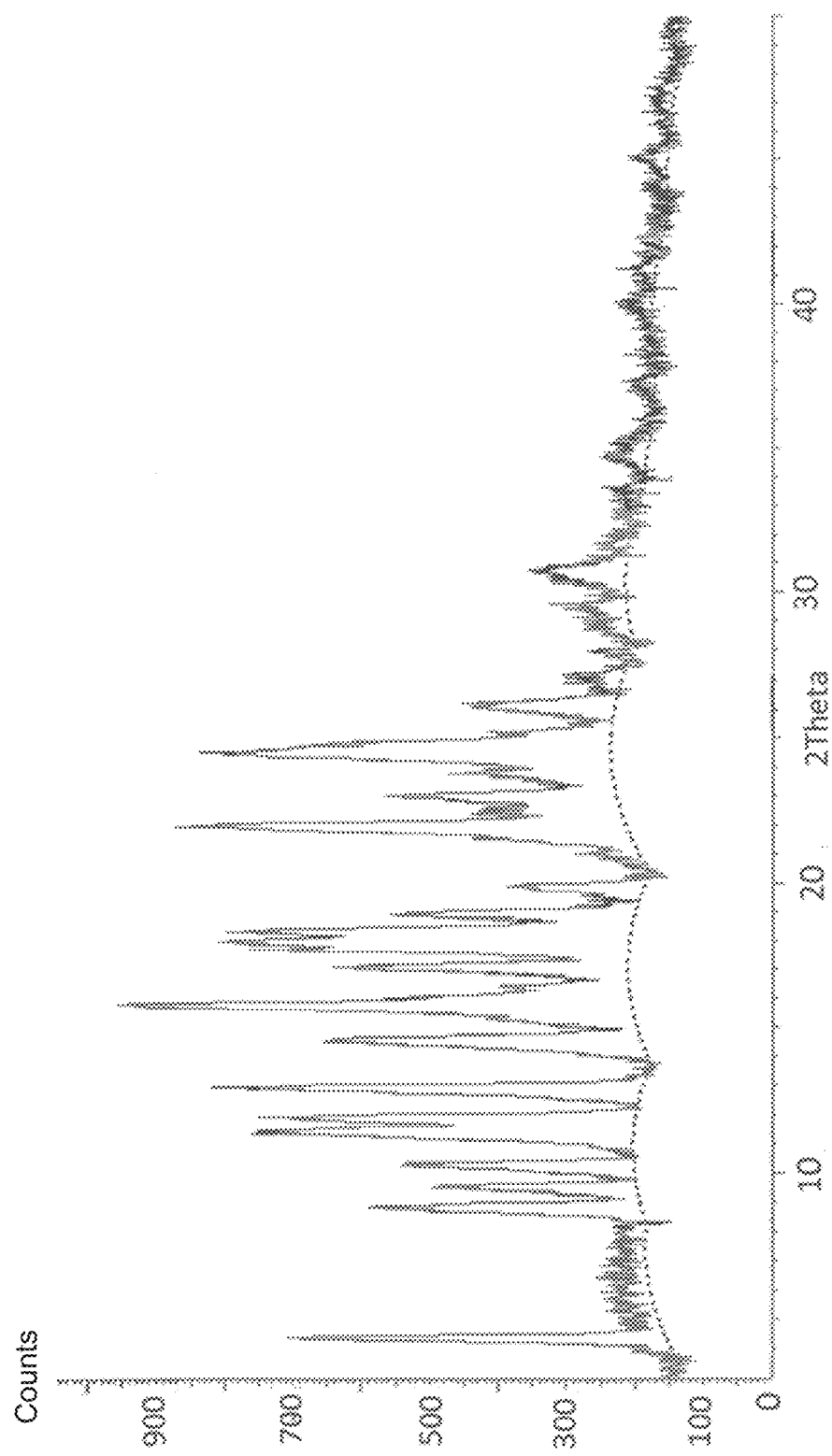
FIG. 4 shows the X-ray powder diffractogram (XRPD) obtained for 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII) of Example 4.

In another preferred embodiment, the compound of formula (VII) in solid form has an X-ray powder diffractogram measured with CuKα radiation essentially as that of FIG. 4.

Figure 6:
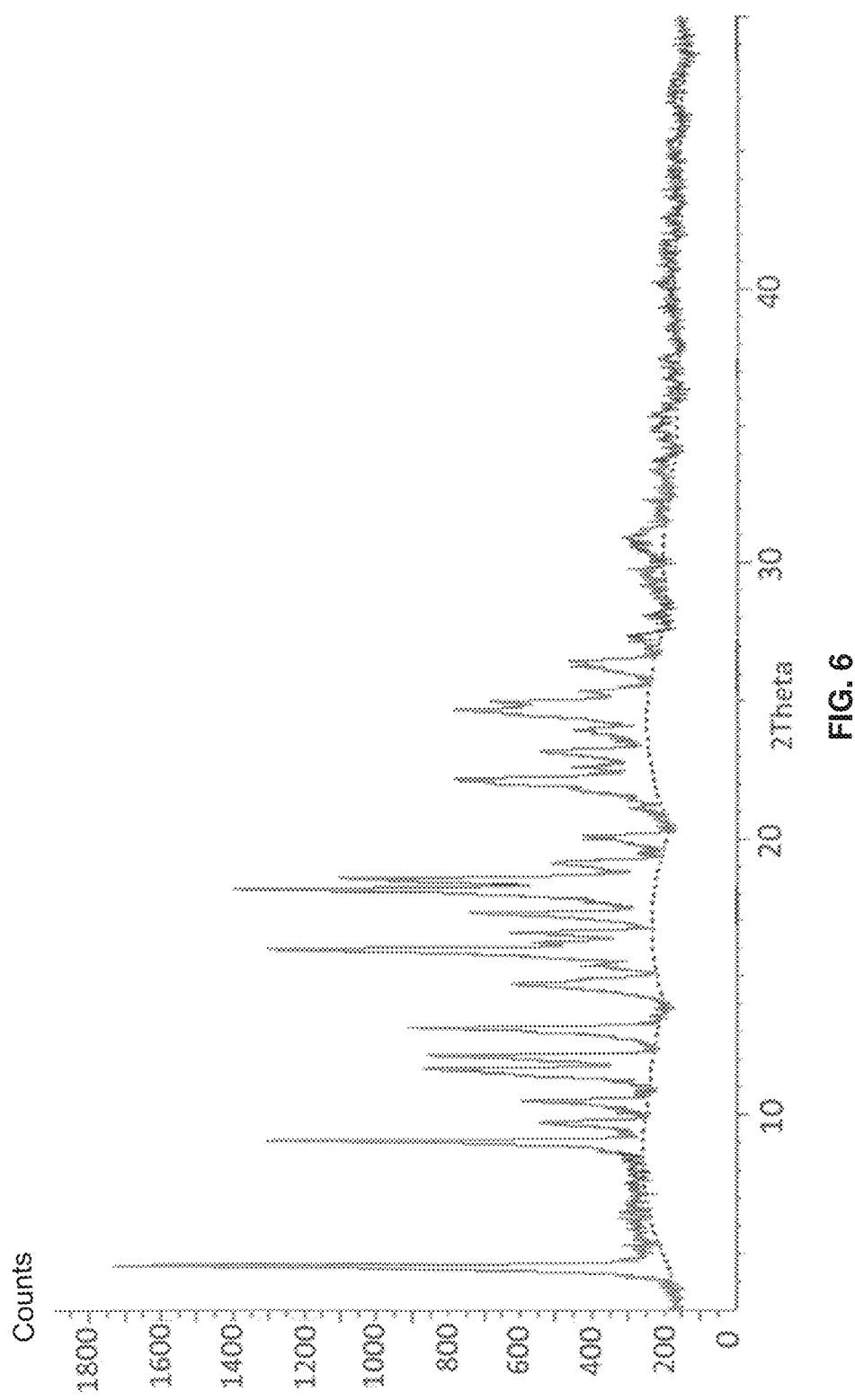
FIG. 6 shows the X-ray powder diffractogram (XRPD) obtained for 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII) of Example 8.

In another preferred embodiment, the compound of formula (VII) in solid form has an X-ray powder diffractogram measured with CuKα radiation essentially as that of FIG. 6.

The X-ray diffractograms can be recorded using a powder diffraction system with a copper anode emitting CuKα radiation with a wavelength of 1.54 Å, in particular, following the method described in the examples.

In a preferred embodiment, the compound of formula (VII) in solid form has a differential scanning calorimetry (DSC) diagram comprising an endothermic peak having an onset temperature of in the range of 170 to 175° C.

Figure 3:
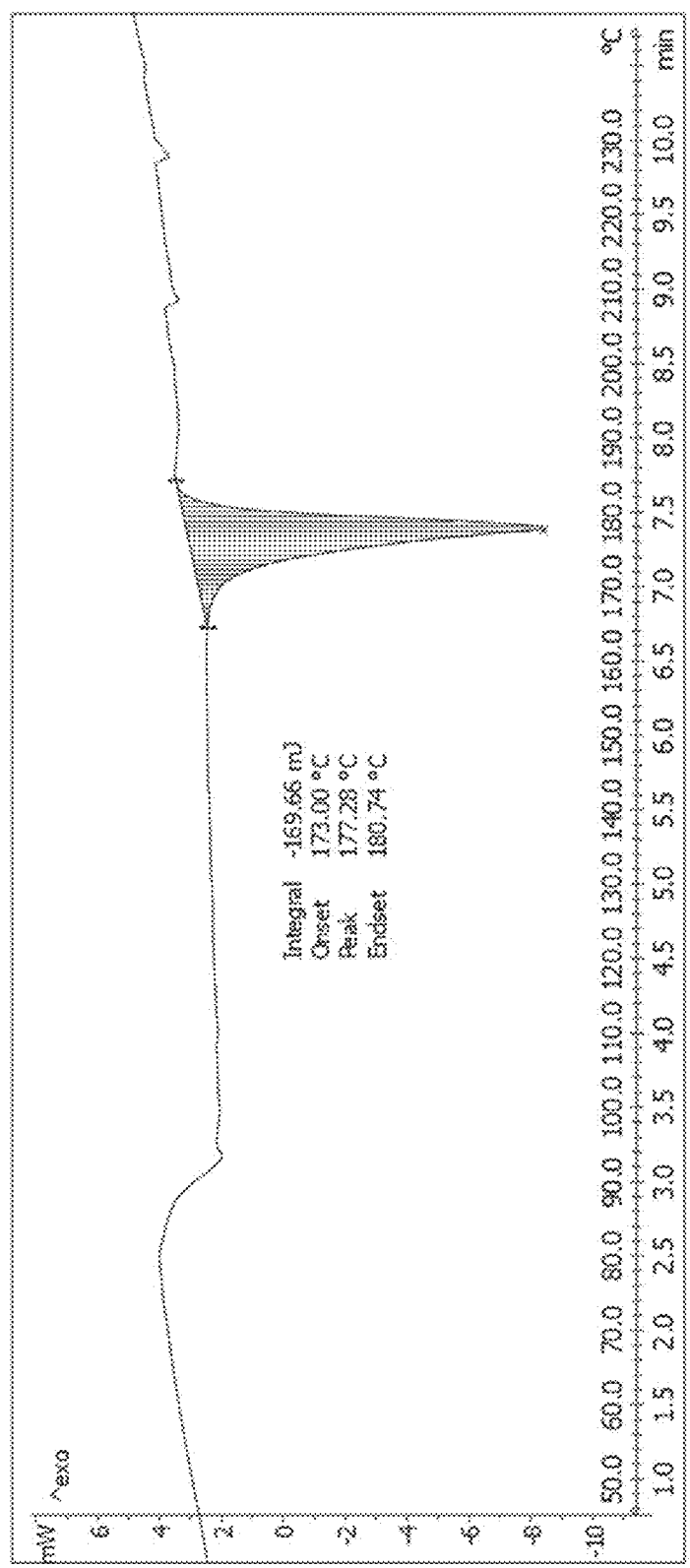
FIG. 3 shows the differential scanning calorimetry (DSC) graph obtained for 3-((R)-2-(amino-2-phenylethyl)-5-(2-fluoro-3-methoxyphenyl)-1-(2-fluoro-6-trifluoromethyl benzyl)-6-methyl-1H-pyrimidine-2,4-dione (VII) of Example 4.

In another preferred embodiment, the compound of formula (VII) in solid form has a differential scanning calorimetry (DSC) diagram essentially as that of FIG. 3.

Figure 5:
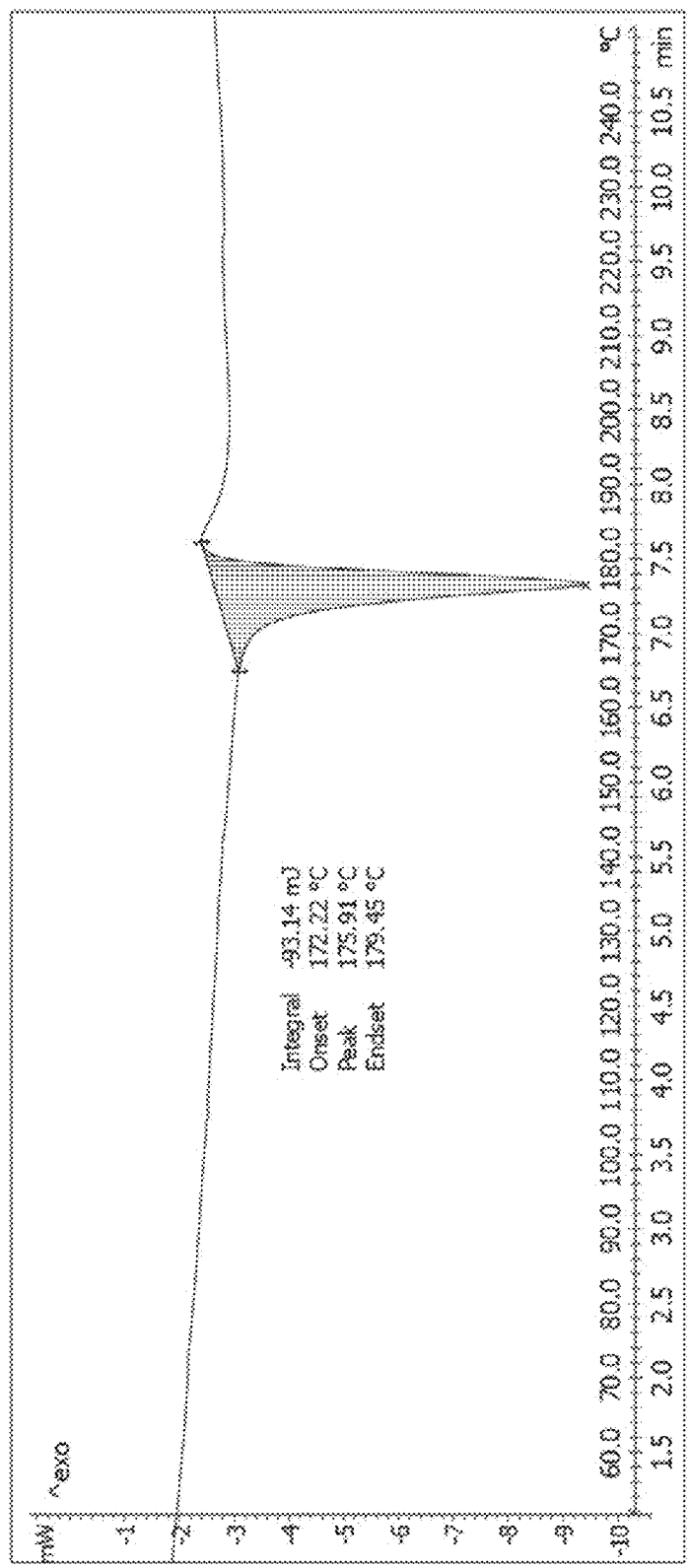
FIG. 5 shows the differential scanning calorimetry (DSC) graph obtained 3-((R)-2-(amino-2-phenylethyl)-5-(2-fluoro-3-methoxyphenyl)-1-(2-fluoro-6-trifluoromethyl benzyl)-6-methyl-1H-pyrimidine-2,4-dione (VII) of Example 8.

In another preferred embodiment, the compound of formula (VII) in solid form has a differential scanning calorimetry (DSC) diagram essentially as that of FIG. 5.

The differential scanning calorimetry diagram can be obtained as described in the examples.

The onset temperature or "T onset" refers to the temperature resulting from extrapolating the baseline before the start of the transition and the baseline during energy absorption (tangent to the curve). It can be calculated as defined in standard DIN ISO 11357-1:2016(E).

In a preferred embodiment, the compound of formula (I) or a salt thereof used in step a) is prepared by a process as defined in the second aspect.

Next, optional steps b1) to b3) can be performed. Said steps, in particular steps b1) and b2), may be performed to increase the purity of 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII) obtained in step a).

In step b1), the 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII) obtained in step a) is treated with HCl to give 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione hydrochloride (VIIa).

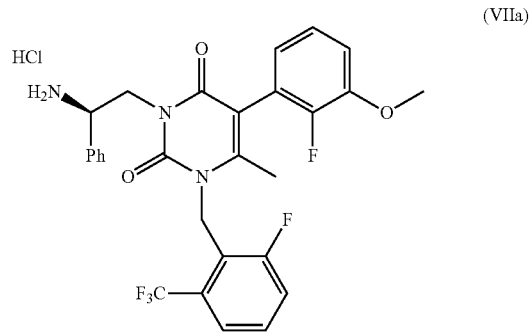 [SMILES: Cl ; COc1cccc(-c2c(C)n(Cc3c(F)cccc3C(F)(F)F)c(=O)n(C[C@H](N)c3ccccc3)c2=O)c1F]

Said treatment is preferably performed with an aqueous solution of HCl and in the presence of an organic solvent, such as, for example, isopropyl acetate. In particular, at least 1 mol of HCl is added with respect to each mol of 3-((R)-

2-(amino-2-phenylethyl)-5-(2-fluoro-3-methoxyphenyl)-1-(2-fluoro-6-trifluoromethylbenzyl)-6-methyl-1H-pyrimidine-2,4-dione (VII), preferably 1 to 3 mol, more preferably 1 to 1.5 mol. In a particular embodiment, the treatment of step b1) is performed at a temperature of 20° C. to 35° C., more preferably 20° C. to 25° C. Preferably, said treatment is performed for 10 min to 60 min.

The treatment of step b1) yields 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione hydrochloride (VIIa), which is isolated in step b2). Said isolation of step b2) can be performed by removing the solvent, preferably by distillation at a pressure of less than Pa (less than 1 atm). In a preferred embodiment, after removing the solvent the hydrochloride (VIa) is crystallized in a suitable organic solvent, such as, for example, 2-methyltetrahydrofuran or tetrahydrofuran (preferably 2-methyltetrahydrofuran). The solid hydrochloride (VIa) obtained is separated from the crystallization solvent, for example by filtration.

Next, step b3) of treating 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione hydrochloride (VIIa) with a base to give 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII), is performed.

In a particular embodiment, the base used in step b3) is selected from the group consisting of diisopropylethylamine, triethylamine, tert-butylamine, and diethylamine, preferably diisopropylethylamine.

In a particular embodiment, step b3) is performed in the presence of an organic solvent, preferably selected from the group consisting of dimethylsulfoxide, toluene, and dimethylformamide, more preferably dimethylformamide.

Step b3) is preferably performed at a temperature in the range of 20° C. to 35° C., more preferably 20° C. to 25° C.

In one embodiment, steps b1)-b3) are performed.

In a preferred embodiment, steps b1)-b3) are not performed.

Next, step c) is of reacting the 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII) obtained in step a) or in step b3) with a $C_{1-4}$ alkyl 4-halobutyrate is performed to obtain a compound of formula (VIII)

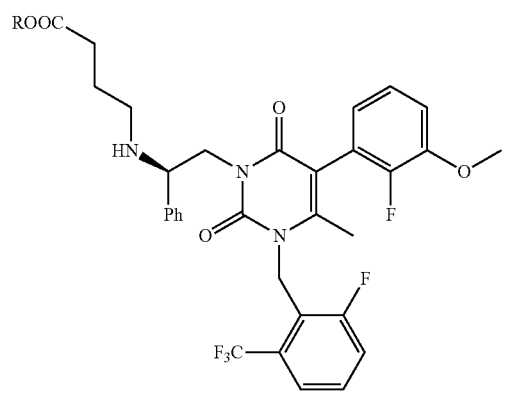

(VIII)

wherein R represents a $C_{1-4}$ alkyl group.

If optional steps b1) to b3) have not been performed, the 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII) obtained in step a) is used in step c). If optional steps b1) to b3) have been performed, the 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII) obtained in step b3) is used in step c). Preferably, steps b1) to b3) are not performed. Therefore, in a preferred embodiment, the 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII) obtained in step a) is used in step c).

The term "halo" in the expression "$C_{1-4}$ alkyl 4-halobutyrate" refers to a halogen atom, i.e., an atom selected from the group consisting of fluorine, chlorine, bromine, and iodine, preferably bromine.

The term "$C_{1-4}$ alkyl" in the expression "$C_{1-4}$ alkyl 4-halobutyrate" refers to a radical having a linear or branched chain consisting of hydrogen atoms and 1 to 4 carbon atoms, with no unsaturations and being bound to the rest of the molecule by means of a single bond. Examples of $C_{1-4}$ alkyl are methyl, ethyl, n-propyl, isopropyl, n-butyl, sec-butyl, iso-butyl, and tert-butyl, preferably ethyl.

In a preferred embodiment, the $C_{1-4}$ alkyl 4-halobutyrate used in step c) is ethyl 4-bromobutyrate, such that the product obtained in said step c) is 4-((R)-2-[5-(2-fluoro-3-methoxyphenyl)-3-(2-fluoro-6-trifluoromethylbenzyl)-4-methyl-2,6-dioxo-3,6-dihydro-2H-pyrimidin-1-yl]-1-phenylethylamino)-butyric acid ethyl ester (VIIIa)

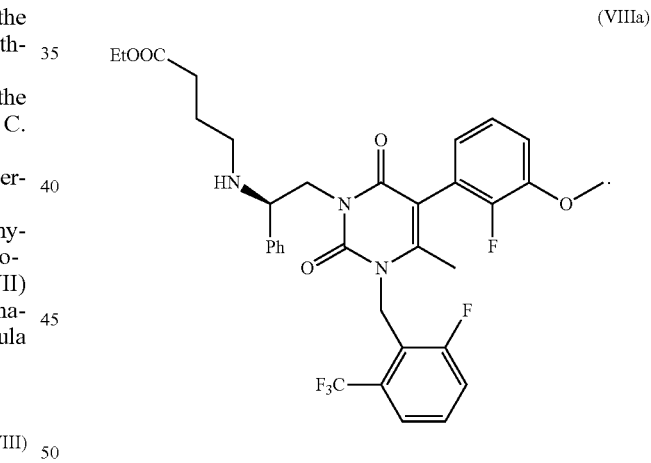

(VIIIa)

In a particular embodiment, at least 1 mol of $C_{1-4}$ alkyl 4-halobutyrate is added with respect to each mol of 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII), preferably 1 to mol, more preferably 1.3 to 1.7 mol.

In a particular embodiment, in step c) a base selected from the group consisting of diisopropylethylamine, triethylamine, tert-butylamine, and diethylamine, preferably diisopropylethylamine, is used.

In a particular embodiment, the reaction in step c) is performed in the presence of a phase-transfer catalyst. Suitable phase-transfer catalysts are quaternary ammonium salts, such as, for example, tetrabutylammonium iodide and tetramethylammonium iodide; preferably the phase-transfer catalyst is tetrabutylammonium iodide (TBAI). In particular, 0.1 to 0.5 mol of phase-transfer catalyst are used with respect to each mol of 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII), preferably 0.15 to 0.25 mol.

In a particular embodiment, step c) is performed at a temperature in the range of 70° C. to 100° C., preferably 80° C. to 90° C., more preferably 80° C. to 85° C. maintaining stirring for a time comprised between 8 and 24 hours, preferably between 8 and 20 hours, more preferably between 12 and 16 hours.

In a particular embodiment, the compound of formula (VIII) obtained in step c) (preferably compound (VIIIa)), is purified before performing step d). In a particular embodiment, purification is performed by i) adding to the reaction medium of step c) water and a water-immiscible organic solvent, preferably isopropyl acetate, ii) treating the organic phase of step i) with an aqueous acid solution, iii) separating said aqueous solution from the organic phase, iv) neutralizing the aqueous solution with a base, v) adding the same solvent mentioned in step i) again, vi) separating the organic phase from said solvent containing the product (VIII), and v) removing the solvent to obtain the product (VIII).

Next, step d) of hydrolysis of the ester group of the compound of formula (VIII) is performed by treatment with NaOH to obtain elagolix sodium (V).

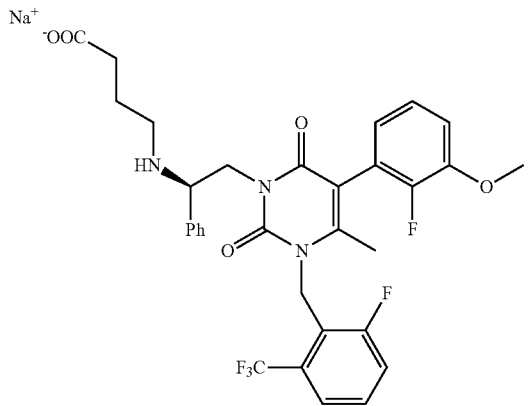

(V)

In a particular embodiment, step d) of hydrolysis is performed in a solvent which is selected from the group consisting of water, $C_1$-$C_4$ alkanol, mixtures of $C_1$-$C_4$ alkanol and water, preferably isopropanol or a mixture of isopropanol and water.

In a particular embodiment, step d) of hydrolysis is performed using as a base an aqueous solution of NaOH at a temperature in the range of 20° C. to 50° C., more preferably 30° C. to 40° C.

In a fourth aspect, the invention relates to the use of a compound of formula (I) or a salt thereof as defined in the first aspect, preferably the hydrochloride (Ia), in a process for preparing elagolix sodium (V).

In particular embodiments of the fourth aspect of the invention, the use of the compound (I) or a salt thereof as defined in the first aspect, preferably the hydrochloride (Ia), is performed following the process described in the third aspect of the invention.

In the context of the present invention, the terms "approximate" and "about" refer to the value these expression characterize ±5% of said value.

In the context of the present invention, the term "acid" refers to a substance capable of donating a proton (to a base).

In the context of the present invention, the term "base" refers to a substance capable of accepting a proton (from an acid).

To help better understand the preceding ideas, several examples of the experimental methods and embodiments of the present invention are described below. Said examples are merely illustrative.

EXAMPLES

Example 1: Obtaining 3-((R)-2-(tert-butoxycarbonyl)amino-2-phenylethyl)-1-(2-fluoro-6-trifluoromethylbenzyl)-6-methyl-1H-pyrimidine-2,4-dione (II)

10 g (33.09 mmol) of 1-(2-fluoro-6-trifluoromethyl-benzyl)-6-methyl-1H-pyrimidine-2,4-dione (III), 6.8 g (49.62 mmol) of $K_2CO_3$ and 2.4 g (6.6 mmol) of tetrabutylammonium iodide were mixed with 50 mL of acetone at the temperature of about 20° C. Subsequently, 13.6 g (43.12 mmol) of (R)-2-((tert-butoxycarbonyl)amino)-2-phenylethyl methanesulfonate (IVa) were added and the obtained mixture was heated at the temperature of about 55° C. and maintained under stirring for about 16 hours at said temperature.

Once this maintenance was finished, the solvent was vacuum distilled and 50 mL of ethyl acetate and 50 mL of water were added to the residue thus obtained. A 1 M aqueous solution of HCl was slowly added, maintaining the temperature between 20 and 25° C. until achieving a pH of between 7 and 8. The aqueous phase was separated and treated with 3 fractions of 30 mL each of ethyl acetate. All the organic extracts were pooled and the solvent was removed by means of vacuum to obtain a slightly yellowish oily residue to which 45 mL of methanol were added, obtaining complete dissolution of the residue.

Example 2: Obtaining 3-((R)-2-(amino-2-phenylethyl)-1-(2-fluoro-6-trifluoromethyl benzyl)-5-iodo-6-methyl-1H-pyrimidine-2,4-dione Hydrochloride Salt (Ia)

16.1 g (99.24 mmol) of iodine monochloride (ICl) were dissolved in 40 mL of methanol at the temperature of about 10° C. The methanol solution previously obtained according to the methodology described in Example 1 comprising 3-((R)-2-(tert-butoxycarbonyl)amino-2-phenylethyl)-1-(2-fluoro-6-trifluoromethylbenzyl)-6-methyl-1H-pyrimidine-2,4-dione (II) was added to the iodine monochloride solution, maintaining the temperature between 20 and 25° C. Once the addition was finished, the obtained solution was heated to about 50° C. and was maintained under stirring for 2 hours at the mentioned temperature.

Once the maintenance was finished, the solvent was vacuum distilled and 50 mL of acetone were slowly added to the obtained oily residue at the temperature of between and 25° C. The addition of acetone caused a solid precipitate to appear almost immediately. The obtained mixture was maintained for 1 hour under stirring at the mentioned temperature. The resulting solid was isolated by filtration, washed with two fractions of 25 mL of acetone, and finally dried at the temperature of 50° C. to obtain 15.6 g (80.8% yield) of a white solid corresponding to the 3-((R)-2-(amino-2-phenylethyl)-1-(2-fluoro-6-trifluoromethylbenzyl)-5-iodo-6-methyl-1H-pyrimidine-2,4-dione hydrochloride salt (Ia) (UHPLC purity: 98.9%).

$^1$H-NMR (d$_6$-DMSO, 400 MHz) δ (ppm): 8.70 (2H, s broad), 7.65-7.48 (3H, m), 7.40-7.32 (5H, m), 5.40-5.29 (2H, dd), 4.47 (1H, t), 4.25 (2H, dd), 2.65 (3H, s).

$^{13}$C-NMR (d$_6$-DMSO, 100 MHz) δ (ppm): 161.87, 159.47, 159.41, 154.19, 150.98, 134.70, 129.93, 129.84, 129.01, 128.58, 127.38, 122.61, 122.34, 122.22, 121.34, 121.10, 74.80, 52.26, 45.45, 44.60, 25.66.

The DSC of this compound is shown in FIG. 1 and the XRPD is shown in FIG. 2.

Example 3: Obtaining 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione Hydrochloride Salt (VIIa)

12.3 g (21.09 mmol) of 3-((R)-2-(amino-2-phenylethyl)-1-(2-fluoro-6-trifluoromethylbenzyl)-5-iodo-6-methyl-1H-pyrimidine-2,4-dione hydrochloride salt (Ia), 4.6 g (27.42 mmol) of 2-fluoro-3-methoxyphenylboronic acid (VI), and 17.9 g (84.36 mmol) of K$_3$PO$_4$·3H$_2$O were dissolved in 74 mL of a 50:50 mixture of acetone/water at the temperature of about 20° C. under nitrogen atmosphere. Subsequently 24 mg (0.1 mmol) of palladium(II) acetate and 62 mg (0.21 mmol) of tri-tert-butyl-tetraphosphonium tetrafluoroborate were added. The mixture thus obtained was heated at the temperature of about 60° C. and maintained at said temperature for 16 hours under nitrogen atmosphere.

Once the maintenance was finished, the reaction mixture was cooled to the temperature of about 20° C., and 50 mL of isopropyl acetate were added. The aqueous phase was separated and treated with 2 fractions of 50 mL each of isopropyl acetate. All the organic extracts were pooled, and 100 mL of water and H$_3$PO$_4$ were added to a pH of the mixture of between 1 and 2. The aqueous phase was separated, and 50 mL of isopropyl acetate were added and, slowly, K$_2$CO$_3$ was also added to a pH of between 9 and 10. The aqueous phase was separated and treated successively with two fractions of 50 mL each of isopropyl acetate. The solvent was removed from the thus pooled organic phases by vacuum distillation to obtain 11.36 g of an orange colored oil comprising 3-((R)-2-amino-2-phenylethyl)-5-(2-fluoro-3-methoxyphenyl)-1-(2-fluoro-6-trifluoromethylbenzyl)-6-methyl-1H-pyrimidine-2,4-dione (VII) (UHPLC purity: 89.9%).

The obtained oil was dissolved in 57 mL of isopropyl acetate, and 1.9 mL of a 12 M aqueous solution of HCl were slowly added, maintaining the temperature between 20 and 25° C. The obtained mixture was maintained under stirring at the indicated temperature for 30 minutes.

Once the maintenance was finished, the solvent was vacuum distilled, and 100 mL of 2-methyltetrahydrofuran were added to the obtained oily residue at the temperature of between 20 and 25° C. The resulting mixture was heated at the reflux temperature and maintained under stirring for 10 minutes. Subsequently, the obtained solution was slowly cooled to an approximate temperature of 20° C., observing the occurrence of a whitish solid. After a maintenance for 30 minutes at the indicated temperature, the resulting solid was isolated by filtration, washed with two fractions of 15 mL of 2-methyltetrahydrofuran, and finally dried at the temperature of 50° C. to obtain 10.8 g (87.8% yield) of a white solid corresponding to the 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione hydrochloride salt (VIIa) (UHPLC purity: 99.03%).

Example 4: Obtaining 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII)

150.0 g (257.0 mmol) of 3-((R)-2-(amino-2-phenylethyl)-1-(2-fluoro-6-trifluoromethylbenzyl)-5-iodo-6-methyl-1H-pyrimidine-2,4-dione hydrochloride salt (Ia), 48.0 g (282.4 mmol) of 2-fluoro-3-methoxyphenylboronic acid (VI), and 205.0 g (769.8 mmol) of K$_3$PO$_4$·3H$_2$O were dissolved in 1200 mL of a 50:50 mixture of acetone/water at the temperature of about 20° C. and nitrogen atmosphere. Subsequently 290 mg (1.3 mmol) of palladium(II) acetate and 750 mg (2.6 mmol) of tri-tert-butyl-tetraphosphonium tetrafluoroborate were added. The mixture thus obtained was heated at the temperature of about 60° C. and was maintained at said temperature for 20 hours under nitrogen atmosphere.

Once the maintenance was finished, the reaction mixture was cooled to the temperature of about 20° C. and the aqueous phase was separated. The solvent was removed from the organic phase by vacuum distillation, and 750 mL of isopropyl acetate and 750 mL of water were added to the obtained residue. The aqueous phase thus obtained was separated and treated with 450 mL of isopropyl acetate. The two organic extracts were pooled, and a solution previously prepared from 50 mL of 85% H$_3$PO$_4$ and from 600 mL of water was added. The aqueous phase was separated, and a solution previously prepared from 20 mL of 85% H$_3$PO$_4$ and from 600 mL of water was added to the organic phase. The aqueous phase thus obtained was separated. The two combined aqueous phases were treated with two fractions of 450 mL of isopropyl acetate. 600 mL of isopropyl acetate and, slowly, K$_2$CO$_3$ were added to the aqueous phase to a pH of about 9. The aqueous phase was separated and treated with 600 mL of isopropyl acetate. The solvent was removed from the thus pooled organic phases by vacuum distillation to obtain 141.2 g of a slightly brown colored solid comprising 3-((R)-2-amino-2-phenylethyl)-5-(2-fluoro-3-methoxyphenyl)-1-(2-fluoro-6-trifluoromethylbenzyl)-6-methyl-1H-pyrimidine-2,4-dione (VII) (UHPLC purity: 94.3%).

The obtained solid was dissolved in 1120 mL of a 50:50 mixture of acetone/water at the temperature of about 20° C. The obtained mixture was heated at the reflux temperature and maintained 15 minutes under stirring. The solution thus obtained was slowly cooled until the occurrence of a solid precipitate (at the temperature of about 50° C.). The mixture was maintained under stirring at the temperature of about 40° C. for 2 hours and was then slowly cooled to the temperature of about 20° C. After a maintenance for 2 hours at the indicated temperature, the resulting solid was isolated by filtration, washed with two fractions of 150 mL each of a 2:1 acetone/water mixture, and finally dried at the temperature of 50° C. to obtain 125.0 g (89.2% yield) of a white solid corresponding to 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII) (UHPLC purity: 99.4%).

The DSC of this compound is shown in FIG. 3 and the XRPD is shown in FIG. 4.

Example 5: Obtaining 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII)

Following the same conditions of the method described in Example 4, starting from 25 g of (42.8 mmol) of 3-((R)-2-

(amino-2-phenylethyl)-1-(2-fluoro-6-trifluoromethylbenzyl)-5-iodo-6-methyl-1H-pyrimidine-2,4-dione hydrochloride salt (Ia), 24.7 g of a solid corresponding to 3-((R)-2-amino-2-phenylethyl)-5-(2-fluoro-3-methoxyphenyl)-1-(2-fluoro-6-trifluoromethylbenzyl)-6-methyl-1H-pyrimidine-2,4-dione (VII) were obtained (UHPLC purity: 94.09%).

The obtained solid was dissolved in 100 mL of acetone and 50 mL of water at the temperature of about 20° C. The obtained mixture was heated at the reflux temperature and maintained 10 minutes under stirring. The solution thus obtained was slowly cooled until the occurrence of a solid precipitate (at the temperature of about 40° C.). The mixture was maintained under stirring at the temperature of about 40° C. for 2 hours and was then slowly cooled to the temperature of about 20° C. After a maintenance for 2 hours at the indicated temperature, the resulting solid was isolated by means of filtration, washed with two fractions of 30 mL each of a 4:2 acetone/water mixture, and finally dried at the temperature of 50° C. to obtain 20.8 g (88.9% yield) of a white solid corresponding to 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII) (UHPLC purity: 99.62%).

Example 6: Obtaining 3-((R)-2-(tert-butoxycarbonyl)amino-2-phenylethyl)-1-(2-fluoro-6-trifluoromethylbenzyl)-6-methyl-1H-pyrimidine-2,4-dione (II)

550 g (1.82 mol) of 1-(2-fluoro-6-trifluoromethyl-benzyl)-6-methyl-1H-pyrimidine-2,4-dione (III) and 914.3 g (6.62 mol) of $K_2CO_3$ were mixed with 2.75 L of N,N-dimethylformamide (DMF) at the temperature of about 20° C. under a nitrogen atmosphere. Subsequently, 918.4 g (2.91 mol) of (R)-2-((tert-butoxycarbonyl)amino)-2-phenylethyl methanesulfonate (IVa) were added and the obtained mixture was heated at the temperature of about 65° C. and maintained under stirring for about 16 hours at said temperature.

Once this maintenance was finished, 5.5 L of tert-butyl methyl ether and 2.75 L of water were added to the reaction mixture maintaining the temperature between 35 and 40° C. The aqueous-DMF phase was separated and treated with one fraction of 2.75 L tert-butyl methyl ether. The aqueous-DMF phase was separated, the two organic extracts were pooled and 2.75 L of water were added. The aqueous phase was separated and 2.75 L of a 2N NaOH aqueous solution was added on the organic phase. The aqueous phase was separated and the solvent of the organic phase was removed by means of vacuum to obtain a yellowish oily residue to which 1425 mL of dichloromethane were added, obtaining complete dissolution of the residue.

Example 7: Obtaining 3-((R)-2-(amino-2-phenylethyl)-1-(2-fluoro-6-trifluoromethyl benzyl)-5-iodo-6-methyl-1H-pyrimidine-2,4-dione Hydrochloride Salt (Ia)

886.48 g (5.46 mol) of iodine monochloride (ICl) were dissolved in 3320 mL of methanol at a temperature between 10 and 20° C. The dichloromethane solution previously obtained according to the methodology described in Example 6 comprising 3-((R)-2-(tert-butoxycarbonyl)amino-2-phenylethyl)-1-(2-fluoro-6-trifluoro methylbenzyl)-6-methyl-1H-pyrimidine-2,4-dione (II) (949.1 g, theoretical) was added to the iodine monochloride solution, maintaining the temperature between 20 and 25° C. Once the addition was finished, the obtained solution was heated to about 50° C. and was maintained under stirring for 3 hours at the mentioned temperature.

Once the maintenance was finished, the solvent was vacuum distilled and 1000 mL of acetone were slowly added to the obtained residue at the temperature of between 20 and 25° C. and the solvent was removed by means of vacuum. 3 L of acetone were added to the residue thus obtained at the temperature of between 20 and 25° C. and the mixture was maintained under stirring for 3 hours at the mentioned temperature. The resulting solid was isolated by filtration, washed with three fractions of 500 mL each of acetone, and finally dried at the temperature of 50° C. to obtain 870.3 g (81.9% yield) of a white solid corresponding to the 3-((R)-2-(amino-2-phenylethyl)-1-(2-fluoro-6-trifluoromethylbenzyl)-5-iodo-6-methyl-1H-pyrimidine-2,4-dione hydrochloride salt (Ia) (UHPLC purity: 98.73%).

Example 8: Obtaining 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII)

750.0 g (1.285 mol) of 3-((R)-2-(amino-2-phenylethyl)-1-(2-fluoro-6-trifluoromethylbenzyl)-5-iodo-6-methyl-1H-pyrimidine-2,4-dione hydrochloride salt (Ia), 240.21 g (1.413 mol) of 2-fluoro-3-methoxyphenylboronic acid (VI), and 1026.59 g (3.855 mol) of $K_3PO_4 \cdot 3H_2O$ were dissolved in 6 L of a 50:50 mixture of acetone/water at the temperature of about 20° C. and under nitrogen atmosphere. Subsequently 1.442 g (6.4 mmol) of palladium(II) acetate and 3.728 g (12.8 mmol) of tri-tert-butyl-tetraphosphonium tetrafluoroborate were added. The mixture thus obtained was heated at the temperature of about 60° C. and was maintained at said temperature for 4 hours under nitrogen atmosphere.

Once the maintenance was finished, the reaction mixture was cooled to the temperature of about 30° C. and the aqueous phase was separated. The solvent was removed from the organic phase by vacuum distillation, and 3750 mL of isopropyl acetate and 3750 mL of water were added to the obtained residue. The aqueous phase thus obtained was separated and treated with 1500 mL of isopropyl acetate. The two organic extracts were pooled, and a solution previously prepared from 250 mL of 85% $H_3PO_4$ and from 2 L of water was added. The aqueous phase was separated, and a solution previously prepared from 50 mL of 85% $H_3PO_4$ and from 2 L of water was added to the organic phase. The aqueous phase thus obtained was separated. The two pooled aqueous phases were treated with two fractions of 2 L each of isopropyl acetate. 3 L of isopropyl acetate were added to the aqueous phase and, slowly, $K_2CO_3$ was also added to a pH of about 8.5. The aqueous phase was separated and treated with 1500 mL of isopropyl acetate. The solvent was removed from the pooled organic phases by vacuum distillation. 750 mL of acetone were added to the residue thus obtained and the solvent was removed by vacuum distillation.

The obtained residue was dissolved in 4.2 L of a 2:1 mixture of acetone/water at the temperature of about 20° C. The obtained mixture was heated at the reflux temperature and maintained 15 minutes under stirring at the indicated temperature. The solution thus obtained was slowly cooled until the occurrence of a solid precipitate (at the temperature of about 50° C.). The mixture was maintained under stirring at the temperature of between 40 and 45° C. for about 2 hours and was then slowly cooled to the temperature of about 20° C. After a maintenance for 2 hours at the indicated temperature, the resulting solid was isolated by filtration, washed with two fractions of 750 mL each of a 2:1 acetone/water mixture, and finally dried at the temperature of 50° C. to obtain 615.4 g (87.8% yield) of a white solid corresponding to 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII) (UHPLC purity: 99.82%).

$^1$H-NMR (d$_6$-DMSO, 400 MHz) δ (ppm): 7.64 (1H, m), 7.52-7.48 (2H, m), 7.28-7.22 (4H, m), 7.20-7.13 (3H, m), 6.73-6.55 (1H, m), 5.29 (2H, s), 4.91-4.83 (1H, m), 4.18-3.93 (3H, m), 3.85 (3H, s), 2.09 (3H, s).

$^{13}$C-NMR (d$_6$-DMSO, 100 MHz) δ (ppm): 166.85, 161.95, 160.41, 159.51, 150.85, 150.83, 150.77, 150.69, 148.34, 147.42, 141.58, 129.73, 128.07, 127.25, 126.93, 124.01, 123.57, 122.57, 121.30, 121.06, 113.38, 106.78, 60.64, 55.95, 47.10, 42.86, 28.84, 18.04.

The DSC of this compound is shown in FIG. 5 and the XRPD is shown in FIG. 6.

Example 9: Obtaining 4-((R)-2-[5-(2-fluoro-3-methoxyphenyl)-3-(2-fluoro-6-trifluoromethylbenzyl)-4-methyl-2,6-dioxo-3,6-dihydro-2H-pyrimidin-1-yl]-1-phenylethyl amino)-butyric Acid Ethyl Ester (VIIIa)

100 g (183.3 mmol) of 3-((R)-2-amino-2-phenylethyl)-5-(2-fluoro-3-methoxyphenyl)-1-(2-fluoro-6-trifluoromethylbenzyl)-6-methyl-1H-pyrimidine-2,4-dione (VII) and 13.54 g of tetrabutylammonium iodide (36.7 mmol) were mixed with 500 mL of isopropyl acetate at the temperature of about 20° C. 120 mL of diisopropylethylamine, subsequently 500 mL of water, and finally 39.5 mL (276.0 mmol) of ethyl 4-bromobutyrate were slowly added. The resulting mixture was heated at the temperature of 80-85° C. and maintained under stirring at said temperature for 16 hours.

Once the maintenance was finished, the reaction mass was cooled at the temperature of about 20° C., and the aqueous phase was separated and treated with 1000 mL of isopropyl acetate. The aqueous phase was separated, and a solution previously prepared from 100 mL of 85% H$_3$PO$_4$ and from 2000 mL of water was added to the pooled organic phases. The aqueous phase was separated, and a solution previously prepared from 40 mL of 85% H$_3$PO$_4$ and from 1000 mL of water was added to the organic phase. The aqueous phase thus obtained was separated. The two combined aqueous phases were treated with 600 mL of isopropyl acetate. The organic phase was separated, and 1500 mL of isopropyl acetate and, slowly, K$_2$CO$_3$ were added to the aqueous phase until a pH of about 8. The aqueous phase was separated and treated with 1000 mL of isopropyl acetate. The thus pooled organic phases were treated with 1000 mL of an aqueous solution of 8% NaHCO$_3$. The solvent was removed from the organic phase thus obtained by means of vacuum distillation to obtain 111.3 g of a residue comprising 4-((R)-2-[5-(2-fluoro-3-methoxyphenyl)-3-(2-fluoro-6-trifluoromethylbenzyl)-4-methyl-2,6-dioxo-3,6-dihydro-2H-pyrimidin-1-yl]-1-phenylethylamino)-butyric acid ethyl ester (VIIIa) (UHPLC: 90.21%).

Example 10: Obtaining 4-((R)-2-[5-(2-fluoro-3-methoxyphenyl)-3-(2-fluoro-6-trifluoro methylbenzyl)-4-methyl-2,6-dioxo-3,6-dihydro-2H-pyrimidin-1-yl]-1-phenylethylamino)-butyric Acid Sodium Salt (V)

The residue obtained in the preceding example comprising 4-((R)-2-[5-(2-fluoro-3-methoxyphenyl)-3-(2-fluoro-6-trifluoromethylbenzyl)-4-methyl-2,6-dioxo-3,6-dihydro-2H-pyrimidin-1-yl]-1-phenylethylamino)-butyric acid ethyl ester (VIIIa) was dissolved in 240 mL of isopropanol. An aqueous solution previously prepared with 18.4 g of NaOH (460.0 mmol) and 240 mL of water was added to said solution at the temperature of about 20° C. The resulting mixture was heated at the temperature of about 35° C. and maintained under stirring at said temperature for 2 hours.

Once the maintenance was finished, the solvent was removed with a vacuum at the maximum temperature of 45° C., and 700 mL of water and 200 mL of isopropyl acetate were added. The aqueous phase was separated and treated with two fractions of 200 mL each of isopropyl acetate. 200 g of NaCl were added, and the pH of the solution was adjusted to about 12 by means of an aqueous solution of 20% NaOH. 500 mL of methyl isobutyl ketone were subsequently added to the treated aqueous phase. The aqueous phase was separated, and two fractions of 500 mL each of methyl isobutyl ketone were added to same. The pooled organic phases were treated with a fraction of 300 mL of an aqueous solution of 20% NaCl. The solvent was removed from the organic phase by vacuum distillation at the maximum temperature of about 45° C., and the obtained residue was dissolved in 500 mL of methyl isobutyl ketone. The obtained mixture was filtered through a filter made up of a layer of diatomaceous earth and a 0.20 micra filter, washing the filter with two fractions of 70 mL each of methyl isobutyl ketone. The filtered solution was slowly added to 2000 mL of heptane, maintaining the temperature at about 20° C. The resulting mixture was maintained under stirring at the indicated temperature for 60 minutes. The resulting solid was isolated by filtration, washed with two fractions of 200 mL each of heptane, and finally dried at the temperature of 40° C. to obtain 89.8 g (75.0% yield) of a virtually white solid corresponding to 4-((R)-2-[5-(2-fluoro-3-methoxyphenyl)-3-(2-fluoro-6-trifluoromethylbenzyl)-4-methyl-2,6-dioxo-3,6-dehydro-2H-pyrimidin-1-yl]-1-phenylethylamino)-butyric acid sodium salt (V) (elagolix sodium salt), with a purity of 99.49% by UHPLC.

Assay Conditions

Analysis by proton nuclear magnetic resonance ($^1$H-NMR) and $^{13}$C-NMR was performed in a 400 MHz Brucker Avance III spectrometer. The chemical shifts are referenced to the DMSO-d$_6$ signal (2.49 ppm for proton and 39.5 ppm for carbon).

DSC analysis was performed in a Mettler Toledo 822e apparatus with STARe SW15 software. Parameters: heating range of 30 to 300° C. with a ramp of 10° C./min and N$_2$ flow of 50 ml/min. The measurement is taken with a perforated closed capsule.

XRPD analysis of compound (Ia) was performed using a Siemens D-500 model X-ray powder diffractometer equipped with a copper anode using Cu K$_α$ radiation. Scanning parameters: 4-50 degrees 2θ, continuous scan, ratio: 1.2 degrees/minute.

XRPD analysis of compound (VII) was performed using a BRUKER D2 PHASER model X-ray powder diffractometer equipped with a copper anode using Cu K$_α$ radiation (1.54060 Å). Scanning parameters: 3-50 degrees 2θ, continuous scan, ratio: 5.6 degrees/minute.

The purity of the obtained products was analyzed by ultra-high-performance liquid chromatography (UHPLC) technique in a Waters Acquity model apparatus, provided with a photodiode detector and thermostated oven for the column. The column used is an HSST3 column (2.1×100 mm and 1.8 μm) and mobile phases A (50 mM ammonium acetate pH 5.2), B (acetonitrile) and C (water) were used with the following analysis conditions:

Flow rate: (mL/min): 0.3
Column T (° C.): 40
Wavelength (nm): 270 (for elagolix), 210 (for the remaining compounds)
Inj. vol. (μL): 1
Acquisition time (min): 10
Diluent: acetonitrile/water (1:1)
Gradient:

| t (min) | % A | % B | % C |
|---------|-----|-----|-----|
| 0       | 5   | 25  | 70  |
| 0.5     | 5   | 25  | 70  |
| 6       | 5   | 90  | 5   |
| 7.5     | 5   | 90  | 5   |
| 8       | 5   | 25  | 70  |
| 10      | 5   | 25  | 70  |

What is claimed is:

1. A compound of formula (I) or a salt thereof

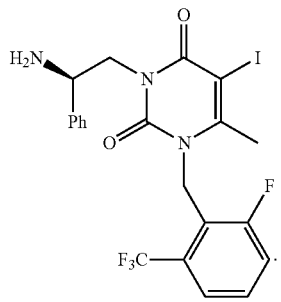

(I)

2. The compound according to claim 1, which is 3-((R)-2-(amino-2-phenylethyl)-1-(2-fluoro-6-trifluoromethylbenzyl)-5-iodo-6-methyl-1H-pyrimidine-2,4-dione hydrochloride (Ia)

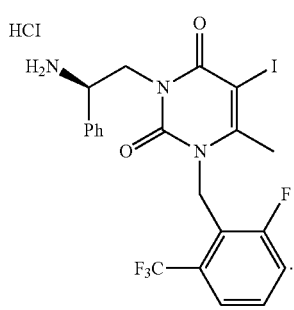

(Ia)

3. 3-((R)-2-(amino-2-phenylethyl)-1-(2-fluoro-6-trifluoromethylbenzyl)-5-iodo-6-methyl-1H-pyrimidine-2,4-dione hydrochloride (Ia) according to claim 2 in a solid form.

4. 3-((R)-2-(amino-2-phenylethyl)-1-(2-fluoro-6-trifluoromethylbenzyl)-5-iodo-6-methyl-1H-pyrimidine-2,4-dione hydrochloride (Ia) according to claim 3, characterized in that it has an X-ray powder diffractogram measured with CuKα radiation comprising peaks at 8.5, 9.9, 14.7, 16.9, 19.5, 21.0, and 22.9° 2θ±0.2° θ.

5. 3-((R)-2-(amino-2-phenylethyl)-1-(2-fluoro-6-trifluoromethylbenzyl)-5-iodo-6-methyl-1H-pyrimidine-2,4-dione hydrochloride (Ia) according to claim 3, characterized in that it has an X-ray powder diffractogram measured with radiation Cu Kα essentially as that of FIG. 2.

6. 3-((R)-2-(amino-2-phenylethyl)-1-(2-fluoro-6-trifluoromethylbenzyl)-5-iodo-6-methyl-1H-pyrimidine-2,4-dione hydrochloride (Ia) according to claim 3, any of claim 3, characterized in that it has a differential scanning calorimetry (DSC) diagram comprising an endothermic peak having an onset temperature of about 240.7° C.±2° C. and an exothermic peak having an onset temperature of about 248.6° C.±2° C.

7. 3-((R)-2-(amino-2-phenylethyl)-1-(2-fluoro-6-trifluoromethylbenzyl)-5-iodo-6-methyl-1H-pyrimidine-2,4-dione hydrochloride (Ia) according to claim 3, characterized in that it has a differential scanning calorimetry (DSC) diagram essentially as that of FIG. 1.

8. A process for preparing a compound of formula (I) or a salt thereof according to claim 1, wherein the process comprises:
   a) reacting 3-((R)-2-(tert-butoxycarbonyl)amino-2-phenylethyl)-1-(2-fluoro-6-trifluoromethylbenzyl)-6-methyl-1H-pyrimidine-2,4-dione (II) with iodine monochloride in the presence of an organic solvent to give 3-((R)-2-(amino-2-phenylethyl)-1-(2-fluoro-6-trifluoromethylbenzyl)-5-iodo-6-methyl-1H-pyrimidine-2,4-dione hydrochloride (Ia)

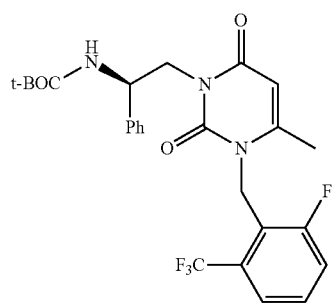

(II)

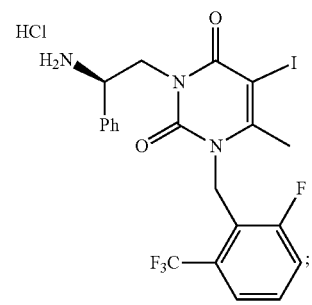

(Ia)

b) optionally treating the 3-((R)-2-(amino-2-phenylethyl)-1-(2-fluoro-6-trifluoromethylbenzyl)-5-iodo-6-methyl-1H-pyrimidine-2,4-dione hydrochloride (Ia) with a base to give the compound of formula (I)

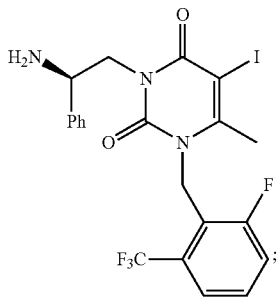
(I)

and c) optionally treating the compound of formula (I) with an acid to give a salt of the compound of formula (I).

9. The process according to claim 8, wherein the organic solvent of said a) is selected from the group consisting of a $C_1$-$C_4$ alkanol, dichloromethane or a mixture thereof.

10. The process according to claim 9, wherein the $C_1$-$C_4$ alkanol is methanol.

11. The process according to claim 8, wherein in said a) 4 to 8 mL of organic solvent are used with respect to each gram of 3-((R)-2-(tert-butoxycarbonyl)amino-2-phenylethyl)-1-(2-fluoro-6-trifluoromethylbenzyl)-6-methyl-1H-pyrimidine-2,4-dione (II).

12. The process according to claim 8, wherein said a) is performed at a temperature of 45° C. to 60° C.

13. The process according to claim 8, wherein in said a) 2 to 4 mol of iodine monochloride are used with respect to each mol of 3-((R)-2-(tert-butoxycarbonyl)amino-2-phenylethyl)-1-(2-fluoro-6-trifluoromethylbenzyl)-6-methyl-1H-pyrimidine-2,4-dione (II).

14. The process according to claim 8, wherein said a) comprises the addition of a solution of 3-((R)-2-(tert-butoxycarbonyl)amino-2-phenylethyl)-1-(2-fluoro-6-trifluoromethylbenzyl)-6-methyl-1H-pyrimidine-2,4-dione (II) in the organic solvent to a solution of iodine monochloride in the organic solvent.

15. The process according to claim 8, wherein said b) and c) are not performed.

16. The process according to claim 8, wherein said b) is performed or wherein said b) and c) are performed.

17. The process according to claim 8, wherein 3-((R)-2-(tert-butoxycarbonyl)amino-2-phenylethyl)-1-(2-fluoro-6-trifluoromethylbenzyl)-6-methyl-1H-pyrimidine-2,4-dione (II) is obtained by reaction of 1-(2-fluoro-6-trifluoromethylbenzyl)-6-methyl-1H-pyrimidine-2,4-dione (III) with a compound of formula (IV), wherein LG is a leaving group, in an organic solvent and in the presence of a base

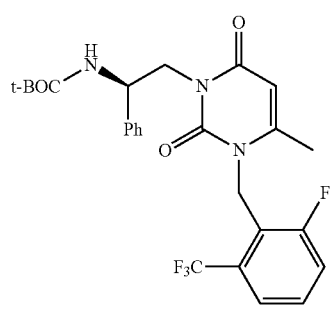
(II)

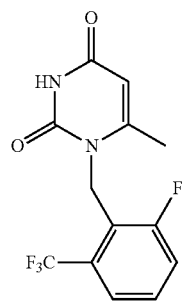
(III)

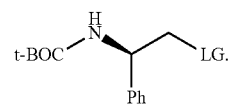
(IV)

18. The process according to claim 17, wherein LG in the compound of formula (IV) is a mesylate group.

19. The process according to claim 17, wherein a phase-transfer catalyst is also used.

20. The process according to claim 19, wherein the phase-transfer catalyst is tetrabutylammonium iodide.

21. The process according to claim 17, wherein the base is $K_2CO_3$.

22. The process according to claim 17, wherein the organic solvent is acetone.

23. A process for preparing elagolix sodium (V) comprising:

a) reacting the compound of formula (I) or a salt thereof according to claim 1 with 2-fluoro-3-methoxyphenylboronic acid (VI) in the presence of a palladium catalyst, a phosphine-type ligand, and a base to give 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII)

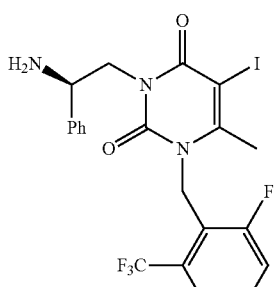
(I)

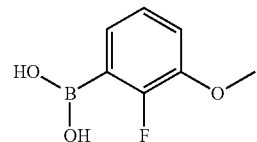
(VI)

(VII)

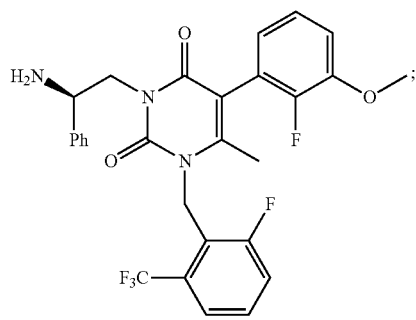

optionally performing b1) to b3):

b1) treating the 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII) with HCl to give 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione hydrochloride (VIIa)

(VIIa)

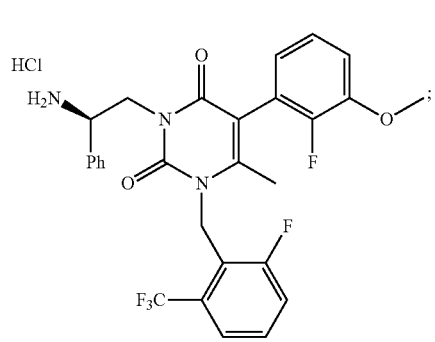

b2) isolating the 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione hydrochloride (VIIa); and b3) treating the 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione hydrochloride (VIIa) with a base to give 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII);

c) reacting the 3-((R)-2-(amino-2-phenylethyl)-5-(2-fluoro-3-methoxyphenyl)-1-(2-fluoro-6-trifluoromethylbenzyl)-6-methyl-1H-pyrimidine-2,4-dione (VII) obtained in said a) or in said b3) with a $C_{1-4}$ alkyl 4-halobutyrate to obtain a compound of formula (VIII)

(VIII)

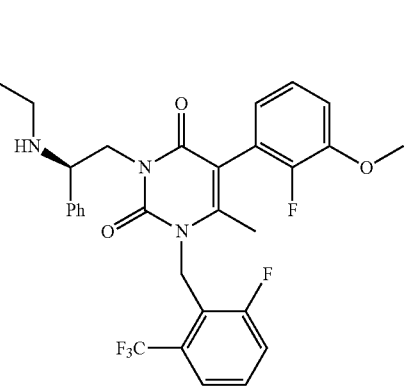

wherein R represents a $C_{1-4}$ alkyl group; and d) hydrolyzing the ester group of the compound of formula (VIII) by treatment with NaOH to obtain elagolix sodium (V)

(V)

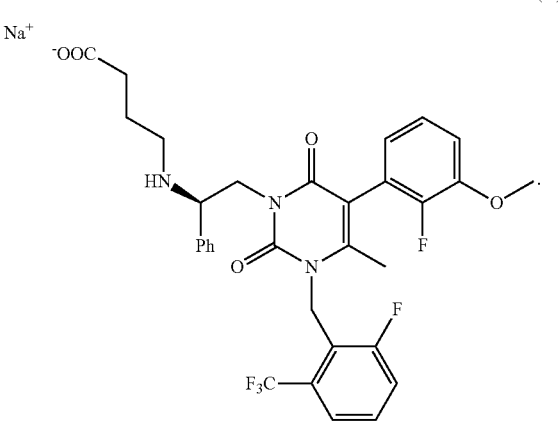

24. The process according to claim 23, wherein the palladium catalyst used in said a) is palladium(II) acetate, the phosphine-type ligand used in said a) is tri-tert-butyltetrafluorophosphonium tetrafluoroborate, and/or the base used in said a) is potassium phosphate or a hydrate thereof.

25. The process according to claim 23, wherein the of $C_{1-4}$ alkyl 4-halobutyrate used in said c) is ethyl 4-bromobutyrate, so that the product obtained in said c) is 4-((R)-2-[5-(2-fluoro-3-methoxyphenyl)-3-(2-fluoro-6-trifluoromethylbenzyl)-4-methyl-2,6-dioxo-3,6-dihydro-2H-pyrimidin-1-yl]-1-phenylethylamino)-butyric acid ethyl ester (VIIIa)

(VIIIa)
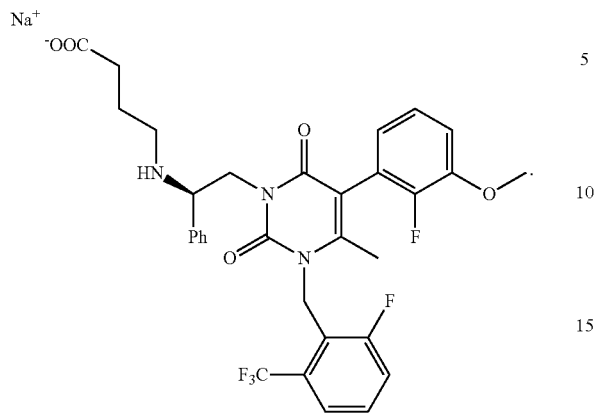
26. The process according to claim 23, wherein said b1) to b3) are not performed.
27. The process according to claim 23, wherein the compound of formula (I) or a salt thereof used in said a) is prepared by the process according to claim 8.
* * * * *